(12) United States Patent
Takebe et al.

(10) Patent No.: US 8,445,019 B2
(45) Date of Patent: May 21, 2013

(54) MICROPARTICLE DISPERSION LIQUID MANUFACTURING METHOD AND MICROPARTICLE DISPERSION LIQUID MANUFACTURING APPARATUS

(75) Inventors: Gen Takebe, Hamamatsu (JP); Tokio Takagi, Hamamatsu (JP); Mitsuo Hiramatsu, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 581 days.

(21) Appl. No.: 12/235,811

(22) Filed: Sep. 23, 2008

(65) Prior Publication Data
US 2009/0081301 A1 Mar. 26, 2009

(30) Foreign Application Priority Data

Sep. 26, 2007 (JP) ................................ P2007-250071
Oct. 1, 2007 (JP) ................................ P2007-257853

(51) Int. Cl.
*A61K 9/10* (2006.01)
*B02C 23/18* (2006.01)

(52) U.S. Cl.
USPC ....................................... 424/489; 241/46.01

(58) Field of Classification Search
None
See application file for complete search history.

(56) References Cited

U.S. PATENT DOCUMENTS

| | | | | |
|---|---|---|---|---|
| 2,578,805 A * | 12/1951 | Johnson | | 241/45 |
| 2005/0241568 A1 | 11/2005 | Sasaki et al. | | |
| 2006/0057219 A1 * | 3/2006 | Nagasaki et al. | | 424/490 |
| 2006/0257489 A1 * | 11/2006 | Kawakami et al. | | 424/489 |
| 2007/0114306 A1 | 5/2007 | Kawakami et al. | | |
| 2007/0152360 A1 * | 7/2007 | Kawakami et al. | | 264/5 |
| 2009/0087460 A1 | 4/2009 | Takebe et al. | | |

FOREIGN PATENT DOCUMENTS

| | | |
|---|---|---|
| CA | 02623112 | 9/2006 |
| JP | 2001-113159 | 4/2001 |
| JP | 2004530111 A | 9/2004 |
| JP | 2005-177596 A | 7/2005 |
| JP | 2005-238342 | 9/2005 |
| JP | 2005-291823 A | 10/2005 |
| JP | 2006-122845 A | 5/2006 |
| JP | 2006-524238 | 10/2006 |
| JP | 2009-079007 A | 4/2009 |
| WO | WO 2007/116632 A1 | 10/2007 |

OTHER PUBLICATIONS

U.S. Appl. No. 13/195,373 and Office action issued on Oct. 30, 2012.*
U.S. Office Action dated Mar. 2, 2011 that issued in U.S. Appl. No. 12/235,825 including a Double Patenting Rejection on pp. 5-7.
U.S. Office Action dated Nov. 10, 2011 that issued in U.S. Appl. No. 13/195,373 including Double Patenting Rejections on pp. 9-11.
U.S. Office Action dated Oct. 11, 2011 that issued in U.S. Appl. No. 12/295,666 including Double Patenting Rejections on pp. 7-9.
U.S. Office Action dated Oct. 28, 2011 that issued in U.S. Appl. No. 13/217,687 including Double Patenting Rejections on pp. 6-9.
U.S. Office Action dated May 7, 2012 that issued in U.S. Appl. No. 12/235,825 including Double Patenting Rejections on pp. 8-11.
U.S. Office Action dated Dec. 7, 2012 that issued in U.S. Appl. No. 12/235,825 including Double Patenting Rejections on pp. 9-11.
U.S. Office Action dated Jun. 5, 2012 that issued in U.S. Appl. No. 12/295,666 including Double Patenting Rejections on pp. 11-12.
U.S. Office Action dated Jun. 7, 2012 that issued in U.S. Appl. No. 13/195,373 including Double Patenting Rejections on pp. 13-15.
U.S. Office Action dated Oct. 24, 2012 that issued in U.S. Appl. No. 12/295,666 including Double Patenting Rejections on pp. 9-11.
U.S. Office Action dated Oct. 30, 2012 that issued in U.S. Appl. No. 13/195,373 including Double Patenting Rejections on pp. 12-13.
Office Action issued on Oct. 25, 2012 in U.S. Appl. No. 13/332,649.

* cited by examiner

*Primary Examiner* — Robert A. Wax
*Assistant Examiner* — H. Sarah Park
(74) *Attorney, Agent, or Firm* — Drinker Biddle & Reath LLP

(57) ABSTRACT

In a dissolving step, a poorly soluble drug and a dispersion stabilizer are dissolved in a volatile organic solvent. In a fixing step, the organic solvent, contained in a solution obtained in the dissolving step, is removed by evaporation, pellet-form residues 1 are obtained by the organic solvent removal, and the residues 1 are fixed on respective bottom surfaces of a plurality of locations of a container 30. In a water injecting step, water 2 is injected into each of a plurality of recesses 31 of the container 30. In an irradiating step, laser light L, emitted from a light irradiating unit 20, is irradiated simultaneously or successively on the residues 1 fixed on the respective bottom surfaces of the recesses 31 of the container 30, and the residues 1 are thereby pulverized and made into microparticles and a microparticle dispersion liquid, constituted of the microparticles being dispersed in the water 2, is manufactured.

2 Claims, 23 Drawing Sheets

2 μm

2 μm

MICROPARTICLE DISPERSION LIQUID MANUFACTURING METHOD AND MICROPARTICLE DISPERSION LIQUID MANUFACTURING APPARATUS

BACKGROUND OF THE INVENTION

1. Field of the Invention

The present invention relates to microparticle dispersion liquid manufacturing method and microparticle dispersion liquid manufacturing apparatus.

2. Related Background Art

In the recent development of new medical drugs, combinatorial chemistry methods have been adopted in synthesizing candidate compounds. Combinatorial chemistry is the art of adopting combinations to synthesize a wide variety of compounds in a short time at one time. Compounds obtained by this method have a solubility problem in many cases. That is, in many cases, even if a compound is found to have excellent physiological activity in itself, if the compound has a property of being difficult to dissolve in water, development of the compound is abandoned. Even with compounds obtained by extraction from natural products, various organic syntheses are carried out and structural optimization is performed to improve solubility. Some medical drugs already on the market are also low in solubility. With such drugs, a drug absorption amount varies within an individual patient and varies among individuals, and this places a large burden in terms of control of levels in blood, etc., on both a physician using a drug and a patient on whom the drug is used.

Microparticle formulations have received attention as a solution to the above problems. With a microparticle formulation, poorly soluble drug particles that are made no more than a micrometer in size are dispersed in water with stability. By using a microparticle formulation, a drug can be increased in absorption rate and amount in a living body. Reduction in variation of absorption amount within an individual patient and among individuals and increase in effective availability with respect to a dose can also be anticipated. Inventions of methods for manufacturing such microparticle formulations are disclosed in Patent Documents 1 and 2.

With the invention disclosed in Patent Document 1, laser light is irradiated on an organic compound, dispersed in a solvent, to obtain ultrafine microparticles of the organic compound. With the invention disclosed in Patent Document 2, ultrashort pulse laser light is irradiated on organic bulk crystals dispersed in a solvent to induce ablation by nonlinear absorption and thereby pulverize the organic bulk crystals into highly dispersed scattered matter, and the highly dispersed scattered matter is collected by the solvent to obtain ultrafine microparticles of an organic compound.

[Patent Document 1] Japanese Published Unexamined Patent Application No. 2001-113159

[Patent Document 2] Japanese Published Unexamined Patent Application No. 2005-238342

SUMMARY OF THE INVENTION

Problem To Be Solved By The Invention

However, with the inventions disclosed in Patent Documents 1 and 2, because the organic compound or the organic bulk crystals to be pulverized are in a state of being dispersed in a solvent, there is a problem that the irradiation of laser light on the organic compound or the organic bulk crystals is incidental and low in processing efficiency.

The present invention has been made to resolve the above problem and an object thereof is provide a method and an apparatus that enable manufacture of a microparticle dispersion liquid at high efficiency in a short time.

Means For Solving The Problem

A method for manufacturing a microparticle dispersion liquid according to the present invention includes: (1) a dissolving step of dissolving a poorly soluble drug and a dispersion stabilizer in a volatile organic solvent; (2) a fixing step of performing removal by evaporation of the organic solvent, contained in a solution obtained in the dissolving step, and fixing a residue, obtained by the organic solvent removal, on each of a plurality of locations of an inner wall of a container; (3) a water injecting step of injecting water into an interior of the container after the fixing step; and (4) an irradiating step of irradiating light on the residues fixed on the respective locations of the inner wall of the container after the water injecting step to manufacture a liquid having microparticles, containing the poorly soluble drug and the dispersion stabilizer, dispersed in water.

A single container may be used throughout the entirety of the dissolving step, fixing step, water injecting step, and irradiating step. The container used in the steps until the residues are obtained and the container used in the steps from the fixing of the residues onward may be separate from each other. Also, a plurality of containers may be used or a single container (such as a microtiter plate), having a plurality of recesses may be used.

With the present microparticle dispersion liquid manufacturing method, the poorly soluble drug and the dispersion stabilizer are dissolved in the volatile organic solvent in the dissolving step. Then, in the subsequent fixing step, the organic solvent, contained in the solution obtained in the dissolving step, is removed by evaporation, and the residues, obtained by the organic solvent removal, are fixed on the respective locations of the inner wall of the container. Water is then injected into the interior of the container in the injecting step that follows. Then, in the irradiating step, the light is irradiated on the residues, fixed on the respective locations of the inner wall of the container, to manufacture the liquid having the microparticles, containing the poorly soluble drug and the dispersion stabilizer, dispersed in water.

With the microparticle dispersion liquid manufacturing method according to the present invention, preferably the container with the plurality of recesses is used to fix the residues on respective bottom surfaces of the recesses in the fixing step, water is injected into each of the recesses of the container in the water injecting step, and, in the irradiating step, the light is irradiated on the residues fixed on the respective bottom surfaces of the recesses of the container. Preferably in this case, the respective bottom surfaces of the recesses of the container are composed of glass, and in the irradiating step, the light is irradiated from outside the respective bottom surfaces of the recesses of the container and the irradiated light is made to propagate in the order of the bottom surfaces, the residues, and the water. Also preferably, the respective bottom surfaces of the recesses of the container are flat surfaces, and in the irradiating step, the light is irradiated from outside the respective bottom surfaces of the recesses of the container and the irradiated light is made to propagate in the order of the bottom surfaces, the residues, and the water.

With the microparticle dispersion liquid manufacturing method according to the present invention, preferably in the irradiating step, light output from a light source is branched by a branching unit and irradiated simultaneously on the residues fixed on the respective locations of the inner wall of the container. Or preferably in the irradiating step, the light output from the light source is diffracted by a diffracting unit and irradiated simultaneously on the residues fixed on the respective locations of the inner wall of the container. Or preferably in the irradiating step, the light output from the light source is scanned by a scanning unit and irradiated successively on the residues fixed on the respective locations of the inner wall of the container.

A microparticle dispersion liquid manufacturing apparatus according to the present invention includes: (1) a container, in which a poorly soluble drug and a dispersion stabilizer are dissolved in a volatile organic solvent, a residue, obtained by removal by evaporation of the organic solvent contained in the solution, is fixed on each of a plurality of locations of an inner wall, and water is injected into an interior; and (2) a light irradiating unit, irradiating light on the residues fixed on the respective locations of the inner wall of the container. Furthermore, with the microparticle dispersion liquid manufacturing apparatus according to the present invention, a liquid, having microparticles, containing the poorly soluble drug and the dispersion stabilizer, dispersed in water, is manufactured by irradiation of the light on the residues by the light irradiating unit.

With the present microparticle dispersion liquid manufacturing apparatus, the poorly soluble drug and the dispersion stabilizer are dissolved in the volatile organic solvent, and the residues, obtained by removal by evaporation of the organic solvent contained in the solution, are fixed on the respective locations of the inner wall of the container, and water is injected into the interior of the container. The light from the light irradiating unit is then irradiated on the residues fixed on the respective locations of the inner wall of the container, and the liquid, having the microparticles, containing the poorly soluble drug and the dispersion stabilizer, dispersed in water, is thereby manufactured.

With the microparticle dispersion liquid manufacturing apparatus according to the present invention, preferably the container has a plurality of recesses, the residues are fixed on respective bottom surfaces of the recesses, and the light irradiating unit irradiates the light on the residues fixed on the respective bottom surfaces of the recesses of the container. Preferably in this case, the respective bottom surfaces of the recesses of the container are composed of glass, the light is irradiated by the light irradiating unit from outside the respective bottom surfaces of the recesses of the container, and the irradiated light is made to propagate in the order of the bottom surfaces, the residues, and the water. Also preferably, the respective bottom surfaces of the recesses of the container are flat surfaces, the light is irradiated by the light irradiating unit from outside the respective bottom surfaces of the recesses of the container, and the irradiated light is made to propagate in the order of the bottom surfaces, the residues, and the water.

Preferably with the microparticle dispersion liquid manufacturing apparatus according to the present invention, the light irradiating unit includes: a light source, outputting light; and a branching unit, branching the light output from the light source and irradiating the light simultaneously on the residues fixed on the respective locations of the inner wall of the container. Or, preferably, the light irradiating unit includes: a light source, outputting light; and a diffracting unit, diffracting the light output from the light source and irradiating the light simultaneously on the residues fixed on the respective locations of the inner wall of the container. Or, preferably, the light irradiating unit includes: a light source, outputting light; and a scanning unit, scanning the light output from the light source and irradiating the light successively on the residues fixed on the respective locations of the inner wall of the container.

Also, a method for manufacturing a microparticle dispersion liquid according to the present invention may include: (1) a dissolving step of dissolving a poorly soluble drug and a dispersion stabilizer in a volatile organic solvent; (2) a fixing step of performing removal by evaporation of the organic solvent, contained in a solution obtained in the dissolving step, and fixing a residue, obtained by the organic solvent removal, on an inner wall of a container; and (3) an irradiating step of injecting water into an interior of the container after the fixing step and, while making the water flow near an interface of the residue and the water in the interior of the container, irradiating light on the residue fixed on the inner wall of the container to manufacture a microparticle dispersion liquid having microparticles, containing the poorly soluble drug and the dispersion stabilizer, dispersed in water.

A single container may be used throughout the entirety of the dissolving step, fixing step, and irradiating step. The container used in the steps until the residue is obtained and the container used in the steps from the fixing of the residue onward may be separate from each other.

With the present microparticle dispersion liquid manufacturing method, the poorly soluble drug and the dispersion stabilizer are dissolved in the volatile organic solvent in the dissolving step. Then, in the subsequent fixing step, the organic solvent, contained in the solution obtained in the dissolving step, is removed by evaporation, and the residue, obtained by the organic solvent removal, is fixed on the inner wall of the container. Then, in the irradiating step that follows, water is injected into the interior of the container, and in a state where the water flows near the interface of the residue and the water in the interior of the container, the light is irradiated on the residue, fixed on the inner wall of the container, to manufacture the liquid having the microparticles, containing the poorly soluble drug and the dispersion stabilizer, dispersed in water.

With the microparticle dispersion liquid manufacturing method according to the present invention, in the irradiating step, the water injected into the interior of the container may be stirred, or the water injected into the interior of the container may be vibrated (preferably vibrated ultrasonically), or water may be fed into the interior of the container, and by any of the above, the water can be made to flow near the interface of the residue and the water in the interior of the container.

With the microparticle dispersion liquid manufacturing method according to the present invention, when in the irradiating step, water is fed into the interior of the container, preferably a temperature of the water fed into the interior of the container is maintained fixed, or preferably the microparticle dispersion liquid manufactured in the interior of the container is collected in a collection container, other than the container, or preferably feeding of water and feeding of a gas into the interior of the container are performed alternately and the microparticle dispersion liquid is collected in the collection container during the feeding of the gas.

Also, a microparticle dispersion liquid manufacturing apparatus according to the present invention includes: (1) a container, in which a poorly soluble drug and a dispersion stabilizer are dissolved in a volatile organic solvent, a residue, obtained by removal by evaporation of the organic solvent contained in the solution, is fixed on an inner wall, and water is injected into an interior; (2) a light irradiating unit, irradiating light on the residue fixed on the inner wall of the container; and (3) a flow unit, making the water flow near an interface of the residue and the water in the interior of the container. Furthermore, with the microparticle dispersion liquid manufacturing apparatus according to the present invention, a microparticle dispersion liquid, having microparticles, containing the poorly soluble drug and the dispersion stabilizer, dispersed in water, may be manufactured by the flow unit making the water flow near the interface of the residue and the water in the interior of the container and the light irradiating unit irradiating the light on the residue.

With the present microparticle dispersion liquid manufacturing apparatus, the poorly soluble drug and the dispersion stabilizer are dissolved in the volatile organic solvent, and the residue, obtained by removal by evaporation of the organic solvent contained in the solution, is fixed on the inner wall of the container. Water is then injected into the interior of the container, the light from the light irradiating unit is irradiated on the residue fixed on the inner wall of the container in the state where the flow unit makes the water flow near the interface of the residue and the water in the interior of the container, and the liquid, having the microparticles, containing the poorly soluble drug and the dispersion stabilizer, dispersed in water, is thereby manufactured.

With the microparticle dispersion liquid manufacturing apparatus according to the present invention, the flow unit may include a stirring unit, stirring the water injected into the interior of the container, or a vibrating unit, vibrating (preferably, ultrasonically vibrating) the water injected into the interior of the container, or a water feeding unit, feeding water into the interior of the container, and by any of these units, the water can be made to flow near the interface of the residue and the water in the interior of the container.

With the microparticle dispersion liquid manufacturing apparatus according to the present invention, preferably when the flow unit includes the above water feeding unit, the water feeding unit maintains the water fed into the interior of the container at a fixed temperature. Or, preferably, a collecting unit, collecting the microparticle dispersion liquid, manufactured inside the interior of the container, is furthermore included. Or, preferably, a gas feeding unit, feeding a gas to the interior of the container, is furthermore included, and the feeding of the water by the water feeding unit and the feeding of the gas by the gas feeding unit are performed alternately and the microparticle dispersion liquid is collected by the collecting unit during the feeding of the gas by the gas feeding unit.

DESCRIPTION OF THE PREFERRED EMBODIMENTS

Best modes for carrying out the present invention shall now be described in detail with reference to the drawings. In the description of the drawings, elements that are the same shall be provided with the same symbols and overlapping description shall be omitted.

Embodiment 1A

Figure 1:
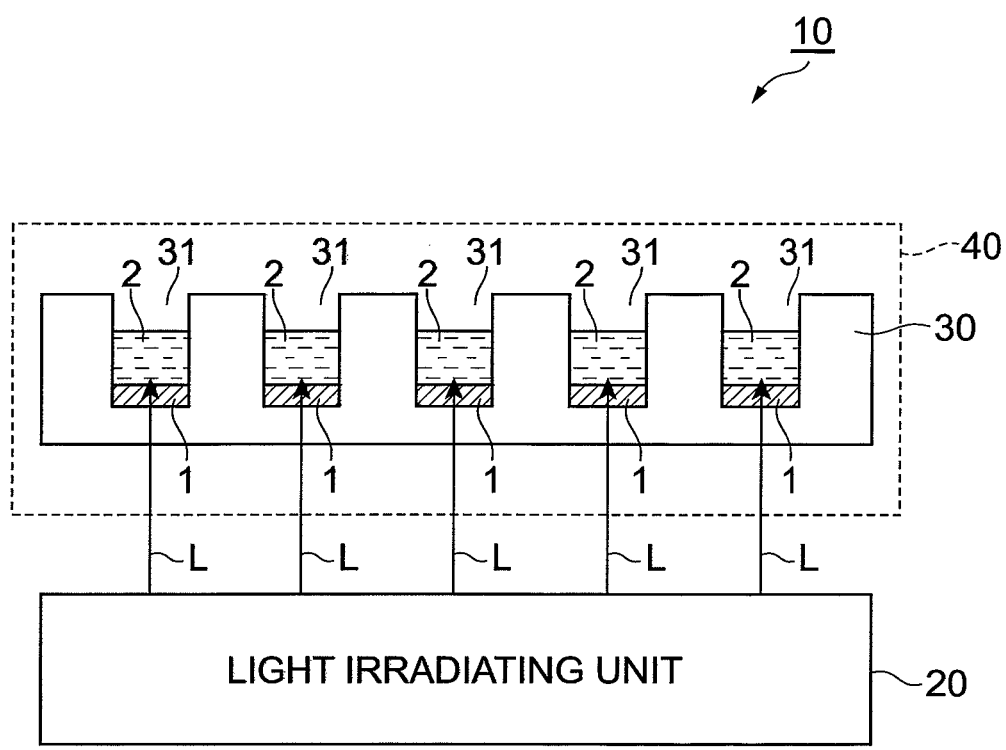
FIG. 1 is a configuration diagram of a microparticle dispersion liquid manufacturing apparatus 10 according to Embodiment 1A.

FIG. 1 is a configuration diagram of a microparticle dispersion liquid manufacturing apparatus 10 according to Embodiment 1A. As shown in this figure, the microparticle dispersion liquid manufacturing apparatus 10 includes a light irradiating unit 20, a container 30, and a temperature controller 40, and is for manufacturing a microparticle dispersion liquid having microparticles, containing a poorly soluble drug and a dispersion stabilizer, dispersed in water.

The container 30 is for containing a liquid to be treated and has a plurality of recesses 31 that are arrayed in one dimension or in two dimensions. A bottom surface of each of the recesses 31 of the container 30 is a flat surface, is composed of a material enabling transmission of a laser light L output from the light irradiating unit 20, and is preferably composed of glass. A microtiter plate is preferably used as the container 30.

The temperature controller 40 includes a constant temperature bath, a thermometer, and a temperature control unit, and maintains the container 30, housed in the constant temperature bath, and the treated liquid, contained in an interior of the container 30, at a fixed temperature by feedback control by the thermometer and the temperature control unit. A portion of the constant temperature bath, through which the laser light L, output from the light irradiating unit 20, passes, is configured as a transparent window.

The light irradiating unit 20 emits the laser light L toward the respective bottom surfaces of the recesses 31 of the container 30 and preferably emits an infrared pulse laser light L with a wavelength of no less than 900 nm. The light irradiating unit 20 preferably can adjust both or either of an intensity and an irradiation duration of the laser light L irradiated on the container 30.

Figure 2:
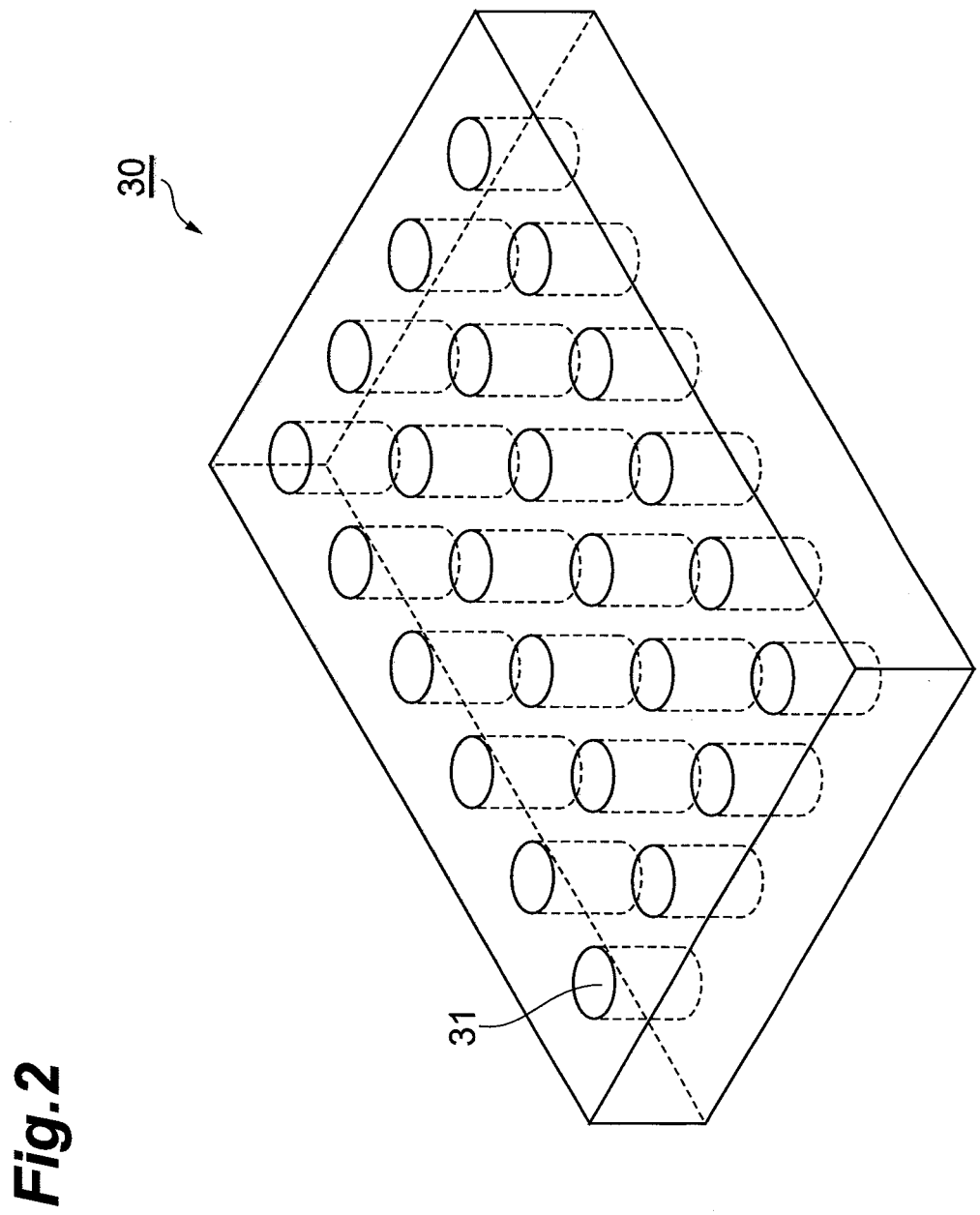
FIG. 2 is a perspective view showing an example of a container 30 used in the microparticle dispersion liquid manufacturing apparatus 10 or a microparticle dispersion liquid manufacturing method according to Embodiment 1A.

FIG. 2 is a perspective view of an example of the container 30 included in the microparticle dispersion liquid manufacturing apparatus 10 according to Embodiment 1A. The container 30 shown in this figure has twenty four of the recesses 31 arrayed two-dimensionally in four rows and six columns. A bottom surface of each of the twenty four recesses 31 is a flat surface and is composed of glass. The twenty four recesses 31 have a common shape and are mutually equal in the thickness of the bottom surface.

Figure 3:
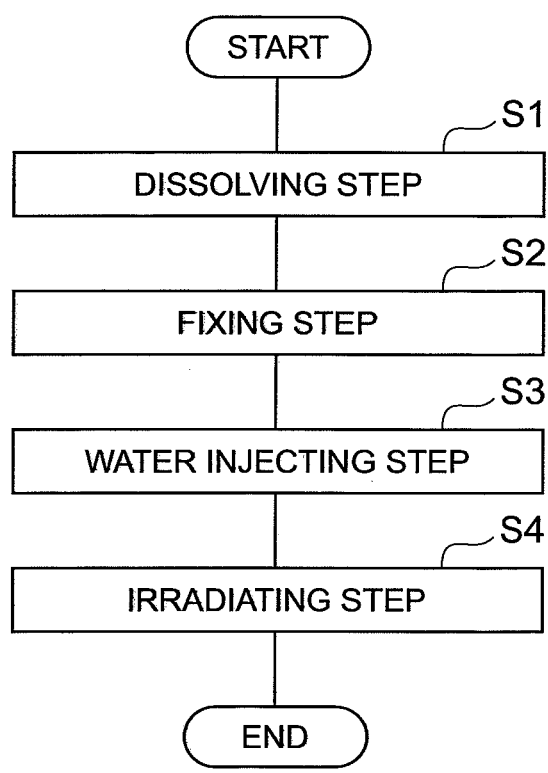
FIG. 3 is a flowchart for describing the microparticle dispersion liquid manufacturing method according to Embodiment 1A.

An operation of the microparticle dispersion liquid manufacturing apparatus 10 according to Embodiment 1A shall now be described along with a method for manufacturing a microparticle dispersion liquid according to Embodiment 1A. FIG. 3 is a flowchart for describing the microparticle dispersion liquid manufacturing method according to Embodiment 1A. With the microparticle dispersion liquid manufacturing method according to Embodiment 1A, a liquid, having microparticles, containing a poorly soluble drug and a dispersion stabilizer, dispersed in water, is manufactured by successively carrying out a dissolving step S1, a fixing step S2, a water injecting step S3, and an irradiating step S4.

In the dissolving step S1, the poorly soluble drug and the dispersion stabilizer are dissolved in a volatile organic solvent. In the dissolving step, the dissolution may be carried out using the container 30 or the dissolution may be carried out using a container other than the container 30.

Here, the poorly soluble drug is a drug that hardly dissolves in water and although a solubility thereof is not restricted in particular, the solubility is preferably no more than 50 μg/mL at a temperature of 25° C. Commercially available drugs, such as cyclosporin, tacrolimus, nifedipine, nicardipine hydrochloride, phenytoin, digitoxin, diazepam, nitrofurantoin, benoxaprofen, griseofulvin, sulfathiazole, piroxicam, carbamazepine, phenacetin, tolbutamide, theophylline, griseofalvin, chloramphenicol, paclitaxel, camptothecine, cisplatin, daunorubicin, methotrexate, mitomycin C, docetaxel, vincristine, amphotericin B, nystatin, ibuprofen, and clobetasone butyrate and other corticosteroids, and other new drug candidate substances under development can be cited as examples of the poorly soluble drug.

The dispersion stabilizer is preferably a high molecular weight polymer or a surfactant. The high molecular weight polymer is preferably a substance that is high in water solubility and is readily soluble in various organic solvents. Hydroxypropylmethylcellulose, methylcellulose, hydroxypropylcellulose, hydroxypropylmethylcellulose phthalate, hydroxypropylmethylcellulose acetate succinate, sodium carboxymethylcellulose, cellulose acetate phthalate, and other cellulose derivatives, agar, gelatin, sodium alginate, polyvinylpyrrolidone, aminoalkylmethacrylate copolymer, methacrylic acid copolymer, carboxyvinyl polymer, polyvinyl alcohol, polyethylene glycol, etc., can be cited as examples of the high molecular weight polymer. The surfactant is preferably of low toxicity, and sodium lauryl sulfate, cholic acid, deoxycholic acid, polyoxyethylene sorbitan fatty acid ester, etc., can be cited as examples.

As the organic solvent, methanol, ethanol, propanol, and other alcohols, acetone, acetonitrile, methyl acetate, ethyl acetate, diethyl ether, etc., can be cited as examples, and methanol, ethanol, propanol, and other alcohols are more preferable.

In the fixing step S2, following the dissolving step S1, the organic solvent contained in the solution obtained in the dissolving step S1 is removed by evaporation, and by the organic solvent removal, pellet-form residues 1 are obtained and the residues 1 become fixed on respective inner walls (bottom surfaces) of a plurality of locations of the container 30. In a case where the dissolution was carried out using a container other than the container 30 in the previous dissolving step S1, the solution is dispensed into each of the recesses 31 of the container 30, the organic solvent is removed by evaporation at each recess 31, and a residue 1 is fixed on the bottom surface of each recess 31. In the water injecting step S3 following the fixing step S2, water 2 is injected into each of the recesses 31 of the container 30. By this water injection, the residues 1, fixed on the respective bottom surfaces of the recesses 31 of the container 30, become immersed in the water 2 (see FIG. 1).

Then, in the irradiating step S4, following the water injecting step S3, the laser light L, emitted from the light irradiating unit 20, is irradiated simultaneously or successively on the residues 1 fixed on the respective bottom surfaces of the recesses 31 of the container 30, the residues 1 are thereby pulverized and made into microparticles, and a microparticle dispersion liquid, in which the microparticles are dispersed in the water 2, is thereby manufactured. The microparticles contain the poorly soluble drug and the dispersion stabilizer.

With the microparticle dispersion liquid manufacturing apparatus 10 according to Embodiment 1A or the microparticle dispersion liquid manufacturing method according to Embodiment 1A, because the laser light L is irradiated at high efficiency on the pellet-form residues 1 fixed on the respective bottom surfaces of the recesses 31 of the container 30, the microparticle dispersion liquid can be manufactured at high efficiency in a short time. Also preferably, an infrared pulse laser light of a wavelength of no less than 900 nm is emitted, and because the microparticles are formed even with a comparatively weak light irradiation of a degree with which multiphoton processes do not occur, drug degradation and other problems can be suppressed. Also with Embodiment 1A, because the laser light L is irradiated simultaneously or successively on the residues 1 fixed on the respective bottom surfaces of the recesses 31 of the container 30 and the microparticle dispersion liquid is manufactured thereby, excellent productivity is realized.

Microparticles, containing the poorly soluble drug and the dispersion stabilizer, are manufactured from the microparticle dispersion liquid manufactured as described above. Or, lyophilized microparticles are manufactured by lyophilizing the microparticle dispersion liquid. Furthermore, an orally administered formulation, containing the microparticle dispersion liquid, the microparticles, or the lyophilized microparticles, is manufactured, or an injection formulation, containing the microparticle dispersion liquid or a dispersion liquid, obtained by resuspending the microparticles or the lyophilized microparticles in water, is manufactured.

Preferably in the irradiating step S4, the laser light L is irradiated from outside region of the inner wall of the container 30 on which the residues 1 are fixed (that is, from a lower side of the respective bottom surfaces of the recesses 31 of the container 30) as shown in FIG. 1 and the irradiated laser light L propagates in the order of the container 30, the residues 1, and the water 2. Microparticles are thereby formed near the interfaces of the residues 1 and the water 2 and these microparticles become immediately dispersed in the water 2. Because the laser light irradiation on the interfaces is constantly performed via the residues 1, even when a high concentration of the microparticles is contained in the water 2, the microparticle formation is not lowered in efficiency and the microparticles are formed at a fixed efficiency.

Preferably in the irradiating step S4, laser light L of a wavelength of no less than 900 nm is irradiated on the residues 1 from the light irradiating unit 20. By the laser light L of such wavelength being irradiated on the residues 1, photodegradation of the drug contained in the residues 1 can be suppressed further. Also, because the laser light L arrives at the interfaces via the residues 1 and the microparticles are formed at the interfaces, laser light L of a wavelength of low absorbance with respect to the residues 1 is preferably irradiated on the residues 1. Specifically, laser light L of a wavelength with which the absorbance with respect to the residues 1 is no more than approximately 0.01 is preferably irradiated.

Preferably in the irradiating step S4, both or either of the intensity and the duration of light irradiation on the residues 1 are or is adjusted, and in this case, it becomes possible to control a particle diameter of the microparticles formed by the light irradiation. Preferably during the light irradiation on the residues 1, the irradiated region or the interior of the container is maintained at a fixed temperature by the temperature controller 40, and in this case, the particle diameter of the microparticles formed by the light irradiation is stabilized.

Preferably a sealed container is used as the container 30, and the dissolving step S1, the fixing step S2, the water injecting step S3, and irradiating step S4 are performed in a sterilized state. Or, the dissolving step S1 may be performed under a non-sterilized state and after filter sterilization of the solution, the fixing step S2, the water injecting step S3, and the irradiating step S4 may be performed in a sterilized state. That is, because Embodiment 1A provides a simple method of simply irradiating light from the exterior of the container 30, it can be put into practice even in a sealed container and an injectable product can also be manufactured readily in a sterilized state.

Figure 4:
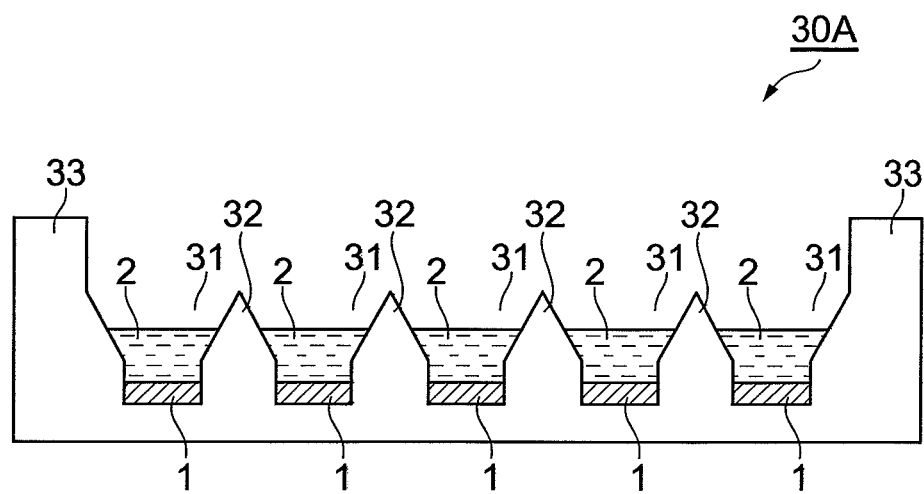
FIG. 4 is a configuration diagram of a modification example of the container 30 used in the microparticle dispersion liquid manufacturing apparatus 10 or the microparticle dispersion liquid manufacturing method according to Embodiment 1A.

FIG. 4 is a configuration diagram of a modification example of the container 30 used in the microparticle dispersion liquid manufacturing apparatus 10 or the microparticle dispersion liquid manufacturing method according to Embodiment 1A. As with the container 30, shown in FIGS. 1 and 2, a container 30A of the modification example shown in FIG. 4 has the plurality of one-dimensionally or two-dimensionally arrayed recesses 31, and with each recess 31, the bottom surface is a flat surface composed of glass. However, in comparison to the container 30, shown in FIGS. 1 and 2, with the container 30A of the modification example shown in FIG. 4, an upper portion of a wall 32 between two mutually adjacent recesses 31 is tapered, and a peripheral wall 33, surrounding the recesses 31, is made higher than the walls 32 between the recesses 31.

The dissolving step S1 can also be performed using the container 30A. That is, in dissolving the poorly soluble drug and the dispersion stabilizer in the volatile organic solvent in the dissolving step S1, by making a liquid level height of the solution higher than the walls 32 and lower than the wall 33, the solution can be obtained in a batch in the container 30A. The fixing step S2 can be performed immediately thereafter. That is, there is no need to use another container, dispensing between the dissolving step S1 and the fixing step S2 is made unnecessary, and the dissolving step S1, the fixing step S2, the water injecting step S3, and the irradiating step S4 can be performed successively. Also, because the upper portions of the walls 32 between the recesses 31 are tapered, the residues 1 can be obtained efficiently at the bottom surfaces of the respective recesses 31 in the fixing step S2.

Configuration examples of the light irradiating unit 20, used in the microparticle dispersion liquid manufacturing apparatus 10 or the microparticle dispersion liquid manufacturing method according to Embodiment 1A shall now be described.

Figure 5:
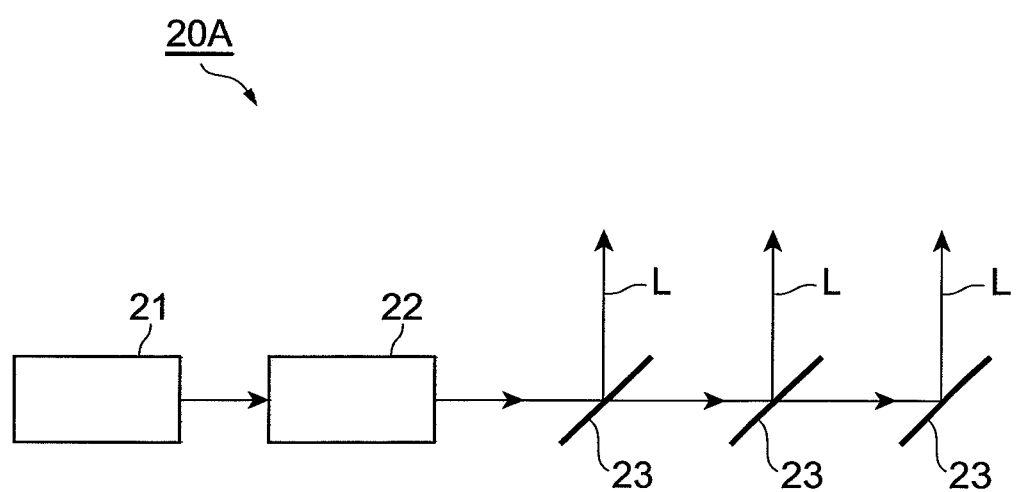
FIG. 5 is a configuration diagram of a light irradiating unit 20A, which is a first configuration example of a light irradiating unit 20.

FIG. 5 is a configuration diagram of a light irradiating unit 20A, which is a first configuration example of the light irradiating unit 20. The light irradiating unit 20A of the first configuration example includes a laser light source 21, an irradiation light controller 22, and a plurality of beam splitters 23. The laser light source 21 outputs laser light. The irradiation light controller 22 adjusts both or either of an intensity and an irradiation duration of the laser light emitted from the laser light source 21. The beam splitters 23 branch the laser light output from the irradiation light controller 22. The beam splitters 23 act as a branching unit that branches the light to simultaneously irradiate the residues 1 fixed on the respective locations of the inner wall of the container 30. The light irradiating unit 20A can irradiate the laser light, branched by the beam splitters 23, simultaneously on the residues 1 fixed on the respective bottom surfaces of the recesses 31 of the container 30. The number of the beam splitters 23 disposed is the same as the number of the recesses 31 of the container 30.

Figure 6:
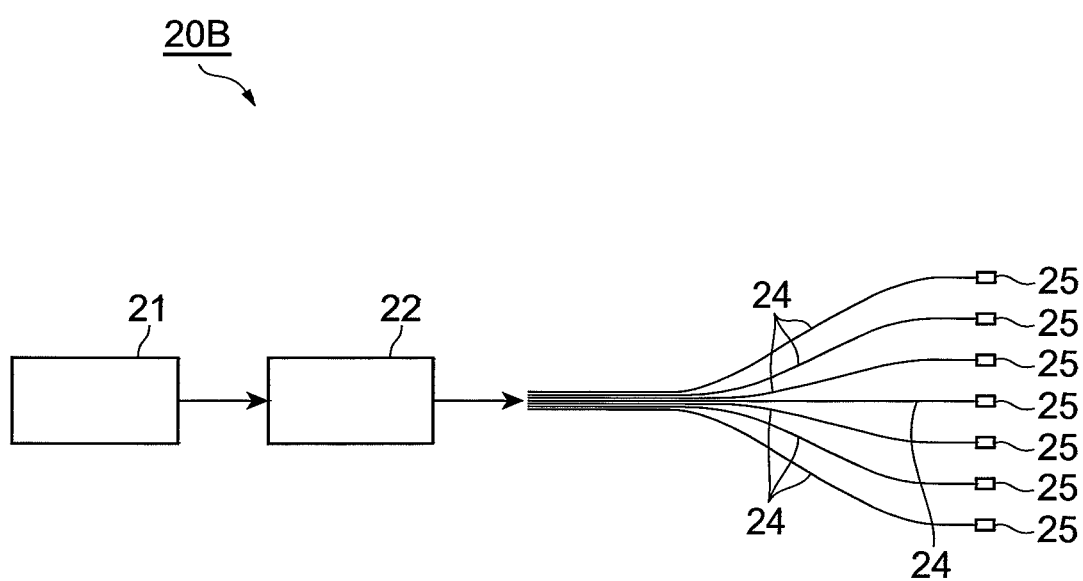
FIG. 6 is a configuration diagram of a light irradiating unit 20B, which is a second configuration example of the light irradiating unit 20.

FIG. 6 is a configuration diagram of a light irradiating unit 20B, which is a second configuration example of the light irradiating unit 20. The light irradiating unit 20B of the second configuration example includes the laser light source 21, the irradiation light controller 22, a plurality of optical fibers 24, and a plurality of collimators 25. Respective light incidence end sides of the optical fibers 24 are bundled together and the laser light output from the irradiation light controller 22 is input simultaneously into the light incidence ends. A collimator 25 is disposed at a light emitting end side of each of the optical fibers 24, and the laser light L is collimated and output simultaneously by the collimators 25. The optical fibers 24 and the collimators 25 act as a branching unit that branches the light to simultaneously irradiate the residues 1 fixed on the respective locations of the inner wall of the container 30. The light irradiating unit 20B can irradiate the laser light, collimated by the respective collimators 25, simultaneously on the residues 1 fixed on the respective bottom surfaces of the recesses 31 of the container 30. The respective numbers of the optical fibers 24 and the collimators 25 disposed are the same as the number of the recesses 31 of the container 30.

Figure 7:
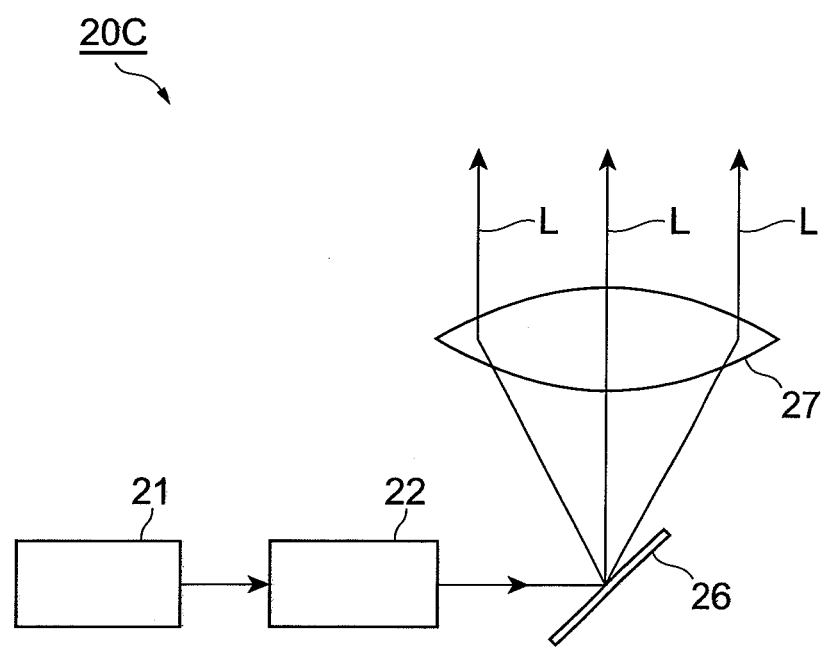
FIG. 7 is a configuration diagram of a light irradiating unit 20C, which is a third configuration example of the light irradiating unit 20.

FIG. 7 is a configuration diagram of a light irradiating unit 20C, which is a third configuration example of the light irradiating unit 20. The light irradiating unit 20C of the third configuration example includes the laser light source 21, the irradiation light controller 22, a diffraction grating 26, and a lens 27. The diffraction grating 26 receives input of the laser light, output from the irradiation light controller 22, and diffracts the laser light at each of a plurality of diffraction orders and outputs a plurality of diffracted light. A distance between the lens 27 and the diffraction grating 26 is equal to a focal length of the lens 27. The lens 27 makes the plurality of diffracted light, output from the diffraction grating 26, parallel to each other. The residues 1 fixed on the inner wall of the container 30 are set between the lens 27 and an imaging plane of the lens according to an irradiation area. The diffraction grating 26 and the lens 27 act as a diffracting unit that diffracts the light to simultaneously irradiate the residues 1 fixed on the respective locations of the inner wall of the container 30. The light irradiating unit 20C can irradiate the plurality of laser light, output from the lens 27, simultaneously on the residues 1 fixed on the respective bottom surfaces of the recesses 31 of the container 30.

In consideration of a size of the container called the microtiter plate, a lens with a long focal length or a lens of large aperture is required to obtain a large diffraction angle. Thus, for example, in a case where a 4×6 or twenty-four well microtiter plate is to be used as the container 30, first, as shown in FIG. 5, 2×3, that is, six beams are formed by beam splitters, and then with each beam, four beams are formed by a diffraction grating as shown in FIG. 7 to obtain a total of twenty four beams. Such a light irradiation method of combining beam splitters and a diffraction grating is extremely preferable.

Figure 8:
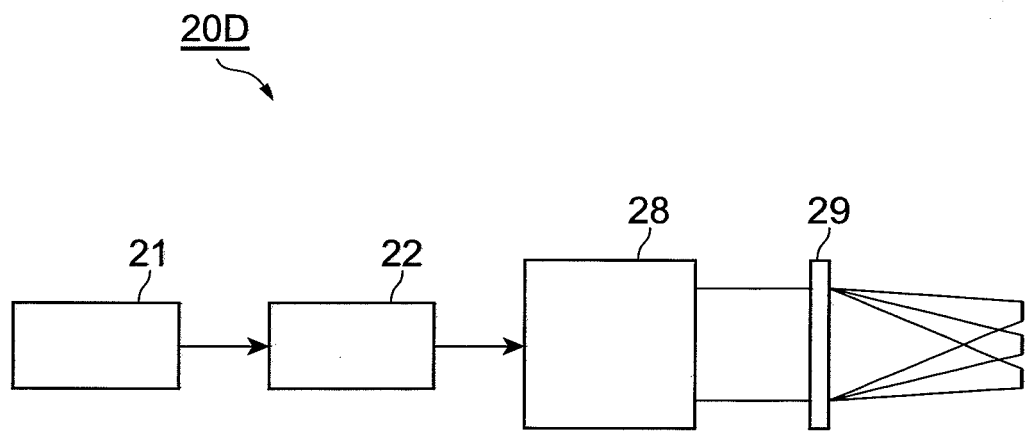
FIG. 8 is a configuration diagram of a light irradiating unit 20D, which is a fourth configuration example of the light irradiating unit 20.

FIG. 8 is a configuration diagram of a light irradiating unit 20D, which is a fourth configuration example of the light irradiating unit 20. The light irradiating unit 20D of the fourth configuration example includes the laser light source 21, the irradiation light controller 22, a beam expander 28, and a spatial optical modulator 29. The beam expander 28 expands a beam cross section of the laser light output from the irradiation light controller 22 and, as necessary, converts a beam cross-sectional shape of the laser light to a rectangular shape. The spatial optical modulator 29 acts as a transmitting or reflecting hologram, receives input of the laser light output from the beam expander 28, modulates an amplitude or phase at respective positions of the beam cross section of the input laser light, and outputs the modulated laser light. The spatial optical modulator 29 acts as a diffracting unit that diffracts the light to simultaneously irradiate the residues 1 fixed on the respective locations of the inner wall of the container 30. The light irradiating unit 20D can irradiate the laser light, output from the spatial optical modulator 29, simultaneously on the residues 1 fixed on the respective bottom surfaces of the recesses 31 of the container 30.

Figure 9:
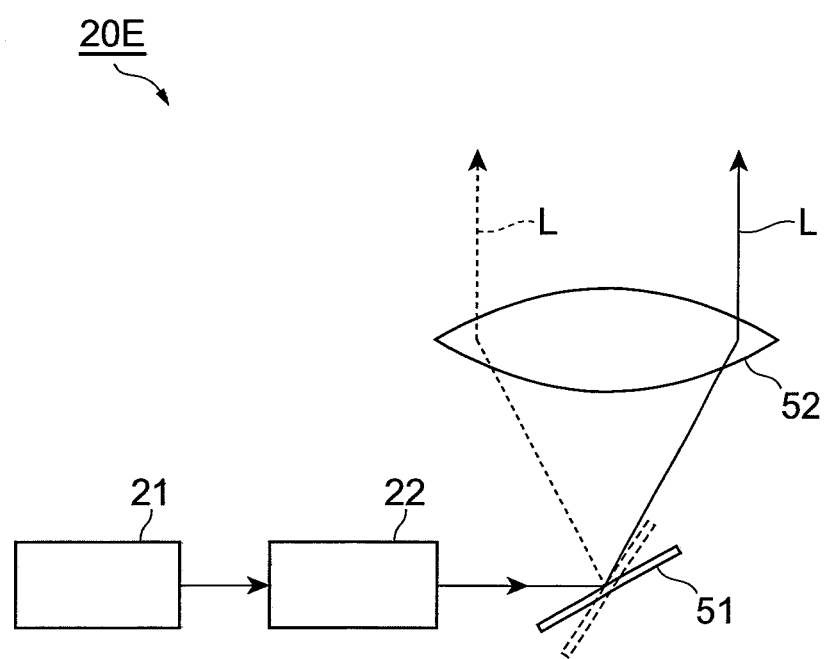
FIG. 9 is a configuration diagram of a light irradiating unit 20E, which is a fifth configuration example of the light irradiating unit 20.

FIG. 9 is a configuration diagram of a light irradiating unit 20E, which is a fifth configuration example of the light irradiating unit 20. The light irradiating unit 20E of the fifth configuration example includes the laser light source 21, the irradiation light controller 22, a movable mirror 51, and a lens 52. The mirror 51 reflects the laser light output from the irradiation light controller 22. A reflecting surface of the mirror 51 can be changed in orientation and reflects the laser light in a direction in accordance with the orientation. A distance between the lens 52 and the movable mirror 51 is equal to a focal length of the lens 52. The lens 52 receives input of the laser light reflected by the movable mirror 51 and outputs the laser light to a predetermined direction. The movable mirror 51 and the lens 52 act as a scanning unit that scans the light to successively irradiate the residues 1 fixed on the respective locations of the inner wall of the container 30. The light irradiating unit 20E can irradiate the laser light L, output from the lens 52, successively on the residues 1 fixed on the respective bottom surfaces of the recesses 31 of the container 30.

Figure 10:
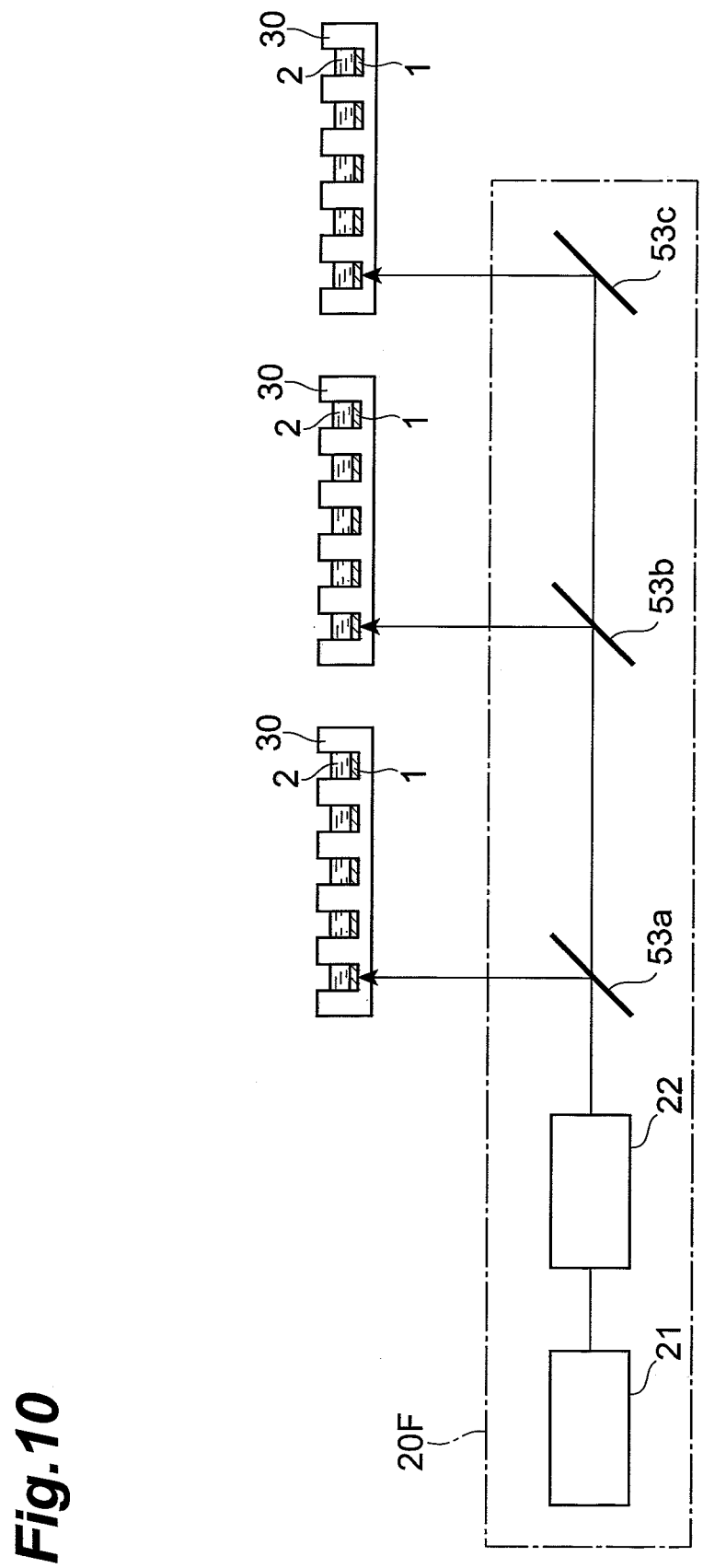
FIG. 10 is a configuration diagram of a light irradiating unit 20F, which is a sixth configuration example of the light irradiating unit 20.

FIG. 10 is a configuration diagram of a light irradiating unit 20F, which is a sixth configuration example of the light irradiating unit 20. In addition to the light irradiating unit 20F of the sixth configuration example, a plurality of the containers 30 are also shown in this figure. The light irradiating unit 20F of the sixth configuration example includes the laser light source 21, the irradiation light controller 22, and a plurality beam splitters 53. The beam splitters 53 branch the laser light output from the irradiation light controller 22. The beam splitters 53 act as a branching unit that branches the light to simultaneously irradiate the residues 1 fixed on any location of the respective inner walls of the containers 30. The containers 30 have a configuration in common, are positioned in parallel, and are enabled to be moved integrally in a direction parallel to the bottom surfaces. With this configuration, by the branching of the laser light by the beam splitters 53, the laser light is irradiated simultaneously on the residues 1 fixed on the any location of the inner walls of the respective containers 30, and by movement of the containers 30, the laser light is irradiated successively on the residues 1 fixed on the respective bottom surfaces of the recesses in the respective containers 30.

Reflectances of the respective beam splitters 53 are determined so that light intensities of the laser light branched by the beam splitters 53 are equal. In FIG. 10, by making the reflectances of the beam splitters 53a, 53b, and 53c approximately 33%, approximately 50%, and approximately 100% respectively, the light intensities of the respective beams are made equal.

Embodiment 1B

Figure 14:
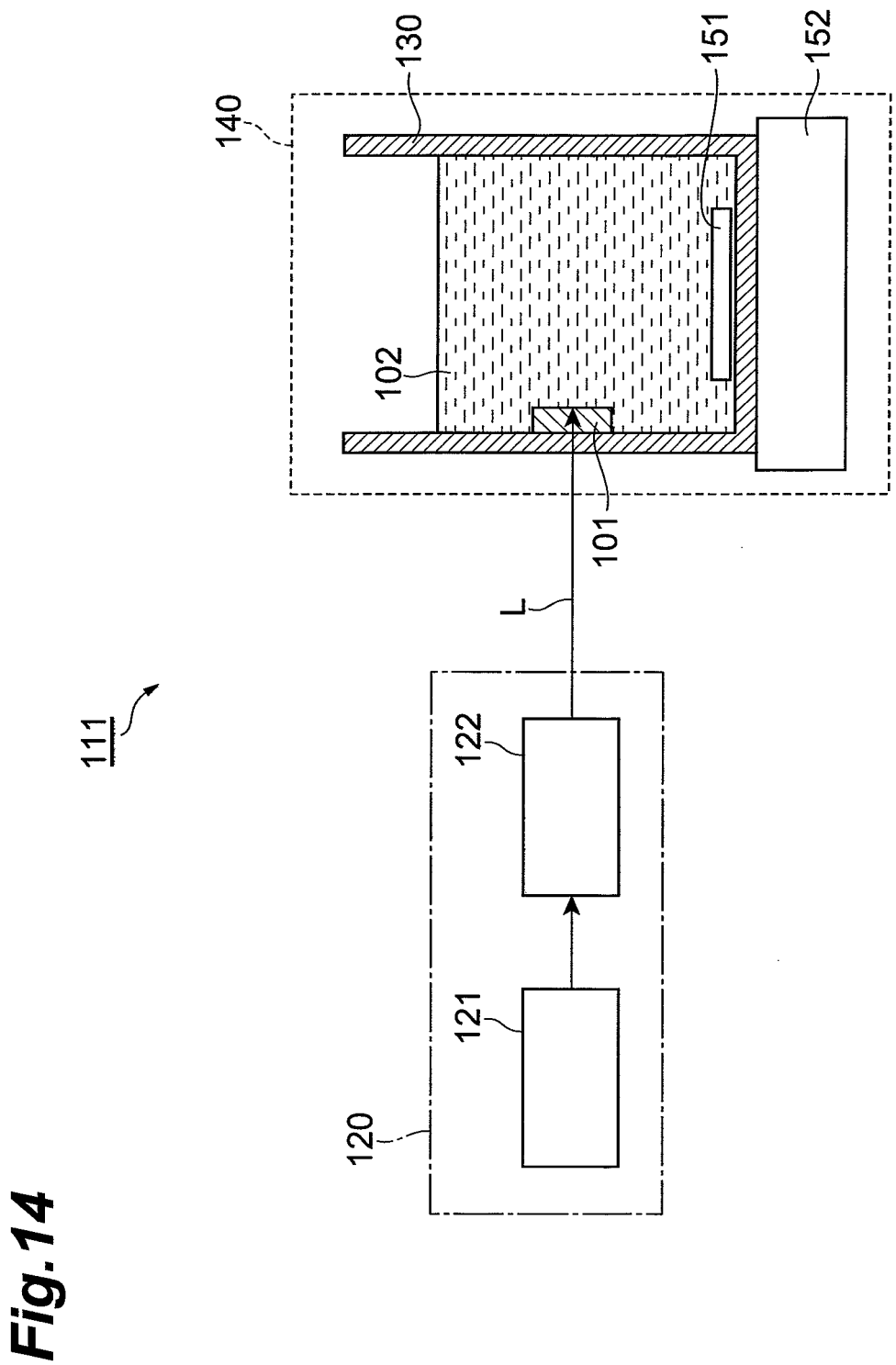
FIG. 14 is a configuration diagram of a microparticle dispersion liquid manufacturing apparatus 111 according to Embodiment 1B.

A microparticle dispersion liquid manufacturing method and a microparticle dispersion liquid manufacturing apparatus according to Embodiment 1B of the present invention shall now be described. FIG. 14 is a configuration diagram of the microparticle dispersion liquid manufacturing apparatus 111 according to Embodiment 1B. As shown in this figure, the microparticle dispersion liquid manufacturing apparatus 111 includes a light irradiating unit 120, a container 130, a temperature controller 140, a magnetic stirrer 151, and a stirrer base 152, and is for manufacturing a microparticle dispersion liquid having microparticles, containing a poorly soluble drug and a dispersion stabilizer, dispersed in water.

The container 130 is for containing a liquid to be treated, is composed of a material enabling transmission of a laser light L output from the light irradiating unit 120, and is preferably composed of quartz glass. In this figure is shown a state where a residue 101, to be described below, is fixed on an inner wall of the container 130 and water 102 is injected into an interior of the container 130.

The temperature controller 140 includes a constant temperature bath, a thermometer, and a temperature control unit, and maintains the container 130, housed in the constant temperature bath, and the treated liquid, contained in the interior of the container 130, at a fixed temperature by feedback control by the thermometer and the temperature control unit. A portion of the constant temperature bath, through which the laser light L, output from the light irradiating unit 120, passes, is configured as a transparent window.

The light irradiating unit 120 emits the laser light L toward the container 130 and includes a laser light source 121 and an irradiation light controller 122. The laser light source 121 preferably emits an infrared laser light L with a wavelength of no less than 900 nm. The irradiation light controller 122 adjusts both or either of an intensity and an irradiation duration of the laser light L emitted from the laser light source 121 and irradiated on the container 130.

The magnetic stirrer 151 is placed in the interior of the container 130 in an irradiating step P3 to be described below, is driven by the stirrer base 152 to rotate above a bottom surface of the container 130, and thereby stirs the water 102 injected into the interior of the container 130 to make the water 102 flow near an interface of the residue 101 and the water 102 in the interior of the container 130. The magnetic stirrer 151 and the stirrer base 152 thus act as a stirring unit that stirs the water 102 injected into the interior of the container 130 and as a flow unit that makes the water 102 flow near the interface of the residue 101 and the water 102 in the interior of the container 130.

Figure 15:
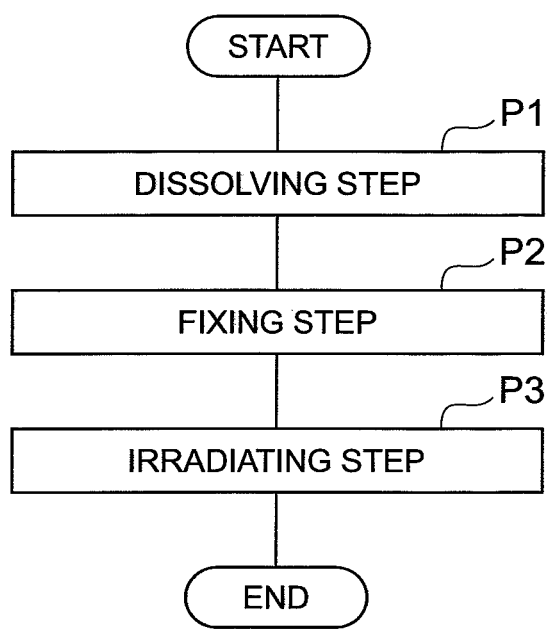
FIG. 15 is a flowchart for describing a microparticle dispersion liquid manufacturing method according to Embodiment 1B.

An operation of the microparticle dispersion liquid manufacturing apparatus 111 according to Embodiment 1B shall now be described along with the microparticle dispersion liquid manufacturing method according to Embodiment 1B. FIG. 15 is a flowchart for describing the microparticle dispersion liquid manufacturing method according to Embodiment 1B. With the microparticle dispersion liquid manufacturing method according to the present embodiment, a microparticle dispersion liquid, having microparticles, containing a poorly soluble drug and a dispersion stabilizer, dispersed in water, is manufactured by successively performing a dissolving step P1, a fixing step P2, and the irradiating step P3.

In the dissolving step P1, the poorly soluble drug and the dispersion stabilizer are dissolved in a volatile organic solvent in the container 130. Here, the poorly soluble drug is a drug that hardly dissolves in water and although a solubility thereof is not restricted in particular, the solubility is preferably no more than 50 µg/mL at a temperature of 25° C. Commercially available drugs, such as cyclosporin, tacrolimus, nifedipine, nicardipine hydrochloride, phenytoin, digitoxin, diazepam, nitrofurantoin, benoxaprofen, griseofulvin, sulfathiazole, piroxicam, carbamazepine, phenacetin, tolbutamide, theophylline, griseofulvin, chloramphenicol, paclitaxel, camptothecine, cisplatin, daunorubicin, methotrexate, mitomycin C, docetaxel, vincristine, amphotericin B, nystatin, and clobetasone butyrate and other corticosteroids, and other new drug candidate substances under development can be cited as examples of the poorly soluble drug.

The dispersion stabilizer is preferably a high molecular weight polymer or a surfactant. The high molecular weight polymer is preferably a substance that is high in water solubility and is readily soluble in various organic solvents. Hydroxypropylmethylcellulose, methylcellulose, hydroxypropylcellulose, hydroxypropylmethylcellulose phthalate, hydroxypropylmethylcellulose acetate succinate, sodium carboxymethylcellulose, cellulose acetate phthalate, and other cellulose derivatives, agar, gelatin, sodium alginate, polyvinylpyrrolidone, aminoalkylmethacrylate copolymer, methacrylic acid copolymer, carboxyvinyl polymer, polyvinyl alcohol, polyethylene glycol, etc., can be cited as examples of the high molecular weight polymer. The surfactant is preferably of low toxicity, and sodium lauryl sulfate, cholic acid, deoxycholic acid, polyoxyethylene sorbitan fatty acid ester, etc., can be cited as examples.

As the organic solvent, methanol, ethanol, propanol, and other alcohols, acetone, acetonitrile, methyl acetate, ethyl acetate, diethyl ether, etc., can be cited as examples, and methanol, ethanol, propanol, and other alcohols are more preferable.

In the fixing step P2, following the dissolving step P1, the organic solvent contained in the solution obtained in the dissolving step P1 is removed by evaporation, and by the organic solvent removal, a pellet-form residue 101 is obtained and the residue 101 becomes fixed on an inner wall of the container 130.

In the irradiating step P3 following the fixing step P2, the water 102 is injected into the interior of the container 130, and the residue 101, fixed on the inner wall of the container 130, becomes immersed in the water 102 (see FIG. 14). Furthermore, in the irradiating step P3, the magnetic stirrer 151, placed in the interior of the container 130, is driven by the stirrer base 152 to rotate above the bottom surface of the container 130, and the water 102 injected into the interior of the container 130 is stirred and the water 102 is thus flows near an interface of the residue 101 and the water 102 in the interior of the container 130.

In the stirred state in the irradiating step P3, the laser light L, output from the laser light source 121 is adjusted in both or either of the intensity and the irradiation duration by the irradiation light controller 122 and irradiated on the residue 101 fixed on the inner wall of the container 130. The stirring by the stirring unit may be performed continuously or intermittently. The residue 101 is thereby pulverized and made into microparticles, and a microparticle dispersion liquid, in which the microparticles are dispersed in the water 102, is thereby manufactured. The microparticles contain the poorly soluble drug and the dispersion stabilizer.

With the microparticle dispersion liquid manufacturing apparatus 111 according to Embodiment 1B or the microparticle dispersion liquid manufacturing method according to Embodiment 1B, because the laser light L is irradiated at high efficiency on the pellet-form residue 101 fixed on the inner wall of the container 130, the microparticle dispersion liquid can be manufactured at high efficiency in a short time. Also preferably, an infrared pulse laser light of a wavelength of no less than 900 nm is emitted, and because the microparticles are formed even with a comparatively weak light irradiation of a degree with which multiphoton processes do not occur, drug degradation and other problems can be suppressed.

Also with the present embodiment, in the irradiating step P3, the water 102, injected into the interior of the container 130, is stirred by the rotation of the magnetic stirrer 151 and the water 102 thus flows near the interface of the residue 101 and the water 102 in the interior of the container 130. The microparticles, formed by the irradiation of the laser light L, are thereby suppressed from being retained or accumulating near the interface of the residue 101 and the water 102. If stirring is not performed, the microparticles become retained or accumulate near the interface of the residue 101 and the water 102, the laser light L becomes scattered by the microparticles, and formation of new microparticles by irradiation of the laser light L is thereby obstructed. However, with the present embodiment, because the microparticles, formed by the irradiation of the laser light L, are suppressed from being retained or accumulating near the interface of the residue 101 and the water 102, the formation of new microparticles by irradiation of the laser light L is not obstructed. Thus, the microparticle dispersion liquid can be manufactured at high efficiency in a short time from this aspect as well.

Microparticles, containing the poorly soluble drug and the dispersion stabilizer, are manufactured from the microparticle dispersion liquid manufactured as described above. Or, lyophilized microparticles are manufactured by lyophilizing the microparticle dispersion liquid. Furthermore, an orally administered formulation, containing the microparticle dispersion liquid, the microparticles, or the lyophilized microparticles, is manufactured, or an injection formulation, containing the microparticle dispersion liquid or a dispersion liquid, obtained by resuspending the microparticles or the lyophilized microparticles in water, is manufactured.

Preferably in the irradiating step P3, the laser light L is irradiated from outside a region of the inner wall of the container 130 on which the residue 101 is fixed as shown in FIG. 14 and the irradiated laser light L propagates in the order of the container 130, the residue 101, and the water 102. Microparticles are thereby formed near the interface of the residue 101 and the water 102 and these microparticles become immediately dispersed in the water 102.

Preferably in the irradiating step P3, laser light L of a wavelength of no less than 900 nm is irradiated on the residue 101 from the light irradiating unit 120. By the laser light L of such wavelength being irradiated on the residue 101, photodegradation of the drug contained in the residue 101 can be suppressed further. Also, because the laser light L arrives at the interface via the residue 101 and the microparticles are formed at the interface, laser light L of a wavelength of low absorbance with respect to the residue 101 is preferably irradiated on the residue 101. Specifically, laser light L of a wavelength with which the absorbance with respect to the residue 101 is no more than approximately 0.01 is preferably irradiated on the residue 101.

Preferably in the irradiating step P3, both or either of the intensity and the duration of light irradiation on the residue 101 are or is adjusted by the irradiation light controller 122, and in this case, it becomes possible to control a particle diameter of the microparticles formed by the light irradiation. Preferably during the light irradiation on the residue 101, the irradiated region or the interior of the container is maintained at a fixed temperature by the temperature controller 140, and in this case, the particle diameter of the microparticles formed by the light irradiation is stabilized.

Preferably a sealed container is used as the container 130, and the dissolving step P1, the fixing step P2, and the irradiating step P3 are performed in a sterilized state. That is, because the present embodiment provides a simple method of simply irradiating light from the exterior of the container 130, it can be put into practice even in a sealed container and an injectable product can also be manufactured readily in a sterilized state.

Modification examples of the container 130 used in the microparticle dispersion liquid manufacturing apparatus 111 according to Embodiment 1B or the microparticle dispersion liquid manufacturing method according to Embodiment 1B shall now be described.

Figure 16:
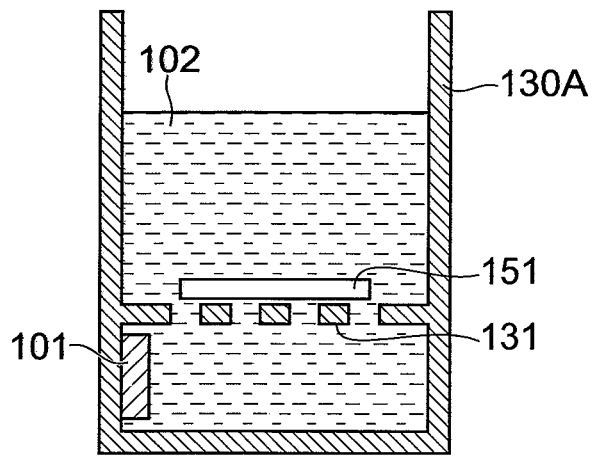
FIG. 16 is a configuration diagram of a first modification example of a container 130 used in Embodiment 1B.

FIG. 16 is a configuration diagram of a first modification example of the container 130 used in Embodiment 1B. In comparison to the container 130, shown in FIG. 14, a container 130A according to the first modification example shown in FIG. 16 differs in that a mesh plate 131 is disposed to partition the interior into upper and lower portions. When the container 130A is used, the pellet-form residue 101, obtained by the organic solvent removal, becomes fixed on the inner wall at a portion of the container 130A lower than the mesh plate 131 in the fixing step P2. In the irradiating step P3, the water 102 is injected to a portion of the container 130A higher than the mesh plate 131 and the magnetic stirrer 151 is positioned on the mesh plate 131. By rotation of the magnetic stirrer 151 on the mesh plate 131, the water 102 below the mesh plate 131 is also stirred and the water 102 flows near the interface of the residue 101 and the water 102. In this stirred state, the laser light L, output from the light irradiating unit 120, is irradiated on the residue 101 fixed on the inner wall of the container 130A.

Figure 17:
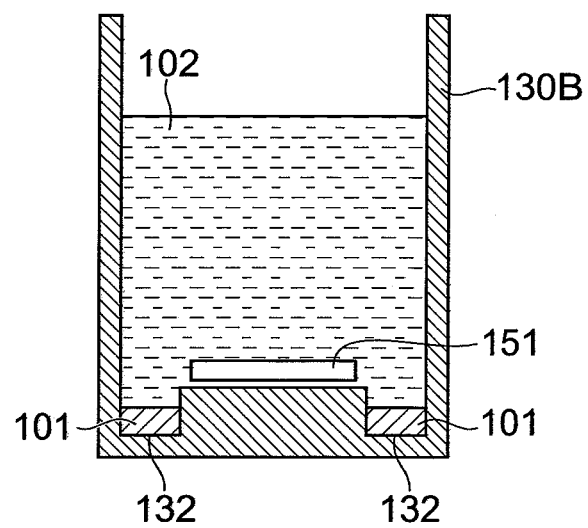
FIG. 17 is a configuration diagram of a second modification example of the container 130 used in Embodiment 1B.

FIG. 17 is a configuration diagram of a second modification example of the container 130 used in Embodiment 1B. In comparison to the container 130, shown in FIG. 14, a container 130B according to the second modification example shown in FIG. 17 differs in that a recess 132 is disposed at an annular region of a circumferential edge portion of the bottom surface. When the container 130B is used, the pellet-form residue 101, obtained by the organic solvent removal, becomes fixed on the peripheral edge recess 132 of the bottom surface of the container 130B in the fixing step P2. In the irradiating step P3, the water 102 is injected into the interior of the container 130, the water 102 is stirred by the rotation of the magnetic stirrer 151, and the water 102 flows near the interface of the residue 101 and the water 102. In this state, the magnetic stirrer 151 does not contact the residue 101. In this stirred state, the laser light L, output from the light irradiating unit 120, is irradiated on the residue 101 fixed on the inner wall of the container 130B.

Even when the containers 130A and 130B of the modification examples are used, because the laser light L is irradiated at high efficiency on the pellet-form residue 101 fixed on the inner wall, the microparticle dispersion liquid can be manufactured at high efficiency in a short time. Also preferably, an infrared pulse laser light of a wavelength of no less than 900 nm is emitted, and because the microparticles are formed even with a comparatively weak light irradiation of a degree with which multiphoton processes do not occur, drug degradation and other problems can be suppressed. Furthermore, because the microparticles, formed by the irradiation of the laser light L, are suppressed from being retained or accumulating near the interface of the residue 101 and the water 102, the formation of new microparticles by irradiation of the laser light L is not obstructed, and the microparticle dispersion liquid can be manufactured at high efficiency in a short time from this aspect as well.

Embodiment 2B

Figure 18:
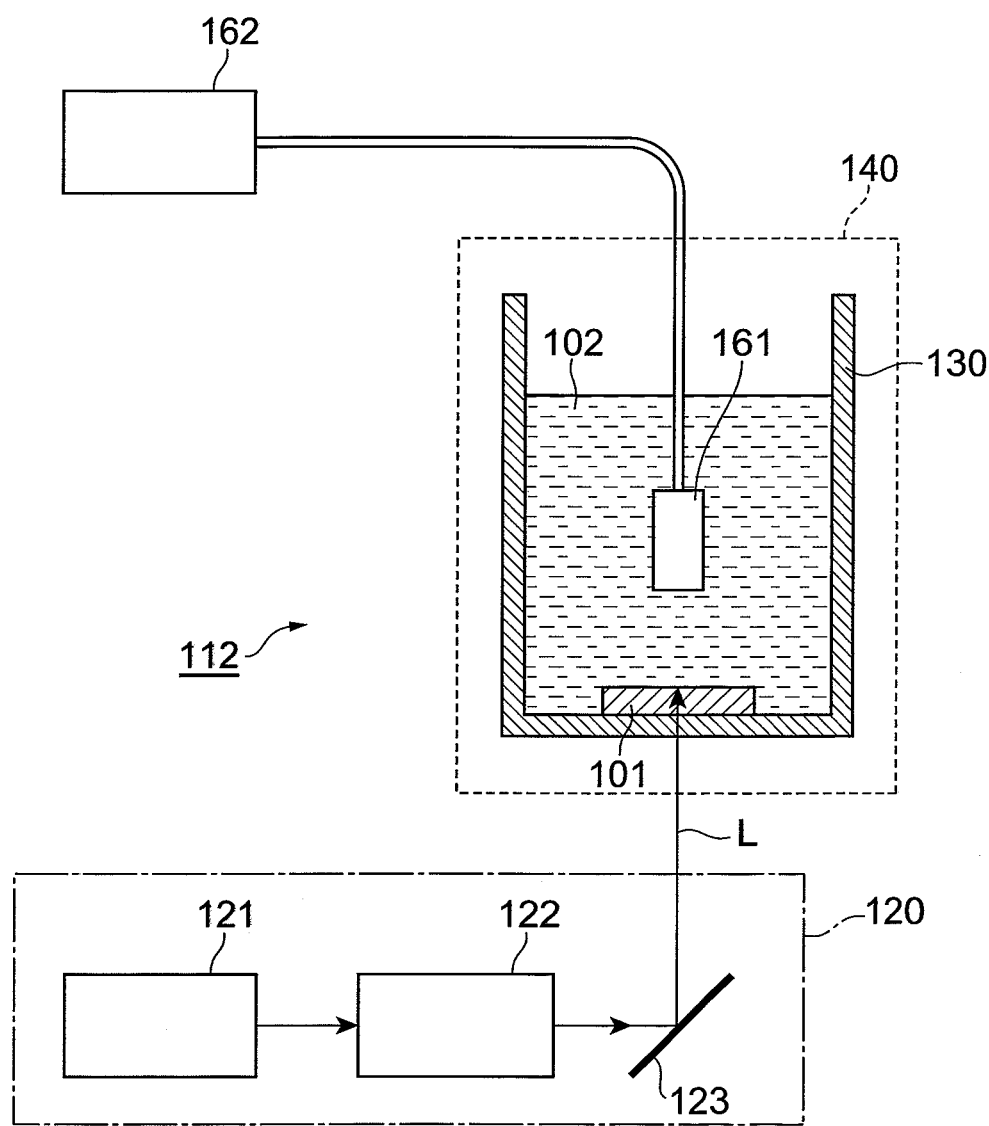
FIG. 18 is a configuration diagram of a microparticle dispersion liquid manufacturing apparatus 112 according to Embodiment 2B.

A microparticle dispersion liquid manufacturing method and a microparticle dispersion liquid manufacturing apparatus according to Embodiment 2B of the present invention shall now be described. FIG. 18 is a configuration diagram of the microparticle dispersion liquid manufacturing apparatus 112 according to Embodiment 2B. As shown in this figure, the microparticle dispersion liquid manufacturing apparatus 112 includes the light irradiating unit 120, the container 130, the temperature controller 140, an ultrasonic probe 161, and a drive unit 162, and is for manufacturing a microparticle dispersion liquid having microparticles, containing a poorly soluble drug and a dispersion stabilizer, dispersed in water.

In comparison to the configuration of the microparticle dispersion liquid manufacturing apparatus 111 according to Embodiment 1B shown in FIG. 14, the microparticle dispersion liquid manufacturing apparatus 112 according to Embodiment 2B shown in FIG. 18 differs in including the ultrasonic probe 161 and the drive unit 162 in place of the magnetic stirrer 151 and the stirrer base 152.

The ultrasonic probe 161 is immersed in the water 102 injected in the interior of the container 130 in the irradiating step P3, is driven by the drive unit 162 to generate ultrasonic waves to ultrasonically vibrate the water 102, injected in the interior of the container 130, and thereby makes the water 102 flow near an interface of the residue 101 and the water 102 in the interior of the container 130. The ultrasonic probe 161 and the drive unit 162 thus act as a vibrating unit that vibrates the water 102 injected into the interior of the container 130 and as a flow unit that makes the water 102 flow near the interface of the residue 101 and the water 102 in the interior of the container 130.

An operation of the microparticle dispersion liquid manufacturing apparatus 112 according to Embodiment 2B shall now be described along with the microparticle dispersion liquid manufacturing method according to Embodiment 2B. A flowchart for describing the microparticle dispersion liquid manufacturing method according to Embodiment 2B is the same as that shown in FIG. 15. A microparticle dispersion liquid, having microparticles, containing a poorly soluble drug and a dispersion stabilizer, dispersed in water, is manufactured by successively performing the dissolving step P1, the fixing step P2, and the irradiating step P3 in the microparticle dispersion liquid manufacturing method according to Embodiment 2B as well. The dissolving step P1 and the fixing step P2 in the present embodiment are respectively the same as those of Embodiment 1B.

In the irradiating step P3 in Embodiment 2B, the water 102 is injected into the interior of the container 130, and the residue 101, fixed on the inner wall of the container 130, becomes immersed in the water 102 (see FIG. 18). Furthermore, in the irradiating step P3, the ultrasonic probe 161, placed in the interior of the container 130, is driven by the drive unit 162 to generate ultrasonic waves, and the water 102 injected into the interior of the container 130 is vibrated and the water 102 is thus flows near the interface of the residue 101 and the water 102 in the interior of the container 130.

In the vibrated state in the irradiating step P3, the laser light L, output from the laser light source 121 is adjusted in both or either of the intensity and the irradiation duration by the irradiation light controller 122, reflected by a mirror 123, and irradiated on the residue 101 fixed on the inner wall of the container 130. The vibration by the vibrating unit may be performed continuously or intermittently. The residue 101 is thereby pulverized and made into microparticles, and a microparticle dispersion liquid, in which the microparticles are dispersed in the water 102, is thereby manufactured. The microparticles contain the poorly soluble drug and the dispersion stabilizer.

With the microparticle dispersion liquid manufacturing apparatus 112 according to Embodiment 2B or the microparticle dispersion liquid manufacturing method according to Embodiment 2B, because the laser light L is irradiated at high efficiency on the pellet-form residue 101 fixed on the inner wall of the container 130, the microparticle dispersion liquid can be manufactured at high efficiency in a short time. Also preferably, an infrared pulse laser light of a wavelength of no less than 900 nm is emitted, and because the microparticles are formed even with a comparatively weak light irradiation of a degree with which multiphoton processes do not occur, drug degradation and other problems can be suppressed.

Also with the present embodiment, in the irradiating step P3, the water 102, injected into the interior of the container 130, is vibrated by the ultrasonic wave generation by the ultrasonic probe 161 and the water 102 thus flows near the interface of the residue 101 and the water 102 in the interior of the container 130. Because the microparticles, formed by the irradiation of the laser light L, are thereby suppressed from being retained or accumulating near the interface of the residue 101 and the water 102, the formation of new microparticles by irradiation of the laser light L is not obstructed. Thus, the microparticle dispersion liquid can be manufactured at high efficiency in a short time from this aspect as well.

Microparticles, containing the poorly soluble drug and the dispersion stabilizer, are manufactured from the microparticle dispersion liquid manufactured as described above. Or, lyophilized microparticles are manufactured by lyophilizing the microparticle dispersion liquid. Furthermore, an orally administered formulation, containing the microparticle dispersion liquid, the microparticles, or the lyophilized microparticles, is manufactured, or an injection formulation, containing the microparticle dispersion liquid or a dispersion liquid, obtained by resuspending the microparticles or the lyophilized microparticles in water, is manufactured.

Preferably in the irradiating step P3, the laser light L is irradiated from outside the region of the inner wall of the container 130 on which the residue 101 is fixed and the irradiated laser light L propagates in the order of the container 130, the residue 101, and the water 102 in the present embodiment as well. Preferably in the irradiating step P3, laser light L of a wavelength of no less than 900 nm is irradiated on the residue 101 from the light irradiating unit 120, and because the laser light L arrives at the interface via the residue 101 and the microparticles are formed at the interface, laser light L of a wavelength of low absorbance with respect to the residue 101 is preferably irradiated on the residue 101. Preferably in the irradiating step P3, both or either of the intensity and the duration of light irradiation on the residue 101 are or is adjusted by the irradiation light controller 122, and preferably during the light irradiation on the residue 101, the irradiated region or the interior of the container is maintained at a fixed temperature by the temperature controller 140. Preferably a sealed container is used as the container 130, and the dissolving step P1, the fixing step P2, and the irradiating step P3 are performed in a sterilized state.

Figure 19:
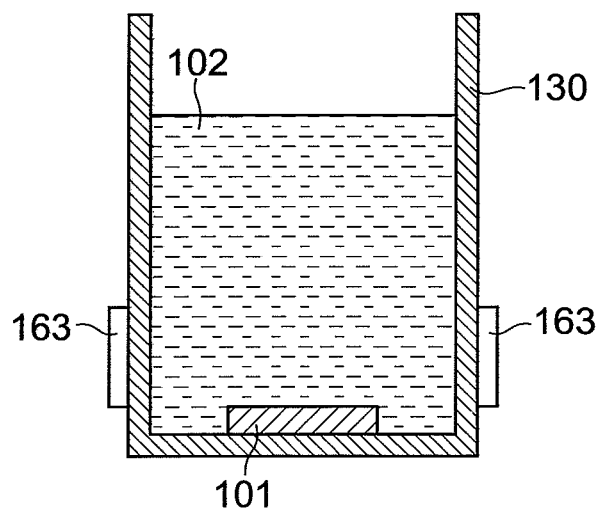
FIG. 19 is a diagram showing a modification example of a vibrating unit used in Embodiment 2B.

A modification example of the vibrating unit used in the microparticle dispersion liquid manufacturing apparatus 112 according to Embodiment 2B or the microparticle dispersion liquid manufacturing method according to Embodiment 2B shall now be described. FIG. 19 is a diagram showing the modification example of the vibrating unit used in Embodiment 2B. With the modification example shown in this figure, ultrasonic generators 163 are adhered as the vibrating unit onto an outer wall of the container 130. Ultrasonic waves generated by the ultrasonic generators 163 are transmitted to the water 102 via the container 130, the water 102, injected into the interior of the container 130, is thereby vibrated ultrasonically, and the water 102 flows near the interface of the residue 101 and the water 102 in the interior of the container 130. Because the microparticles, formed by the irradiation of the laser light L, are thereby suppressed from being retained or accumulating near the interface of the residue 101 and the water 102, the formation of new microparticles by irradiation of the laser light L is not obstructed and the microparticle dispersion liquid can be manufactured at high efficiency in a short time.

As a modification example of the vibrating unit in Embodiment 2B, an ultrasonic cleaner (for example, B5510, manufactured by Branson Ultrasonics Corp.) may be used and the container 130 may be placed in the ultrasonic cleaner to ultrasonically vibrate the water in the interior of the container 130. Or, as a modification example of the vibrating unit in Embodiment 2B, a test tube mixer (for example, HM-10H manufactured by As One Corp.) may be used and the container 130 may be placed in the test tube mixer to vibrate the water in the interior of the container 130. The water 102 vibrates and the water 102 flows near the interface of the residue 101 and the water 102 in the interior of the container 130 in these cases as well. Because the microparticles, formed by the irradiation of the laser light L, are thereby suppressed from being retained or accumulating near the interface of the residue 101 and the water 102, the formation of new microparticles by irradiation of the laser light L is not obstructed and the microparticle dispersion liquid can be manufactured at high efficiency in a short time.

With Embodiment 2B, the residue 101 fixed on the inner wall of the container 130 is made into microparticles not only by being pulverized by the application of light energy by the laser light irradiation but is also made into microparticles by being pulverized by the application of vibration energy in some cases. Thus, with Embodiment 2B, the microparticle dispersion liquid can be manufactured at high efficiency in a short time from this aspect as well.

Embodiment 3B

Figure 20:
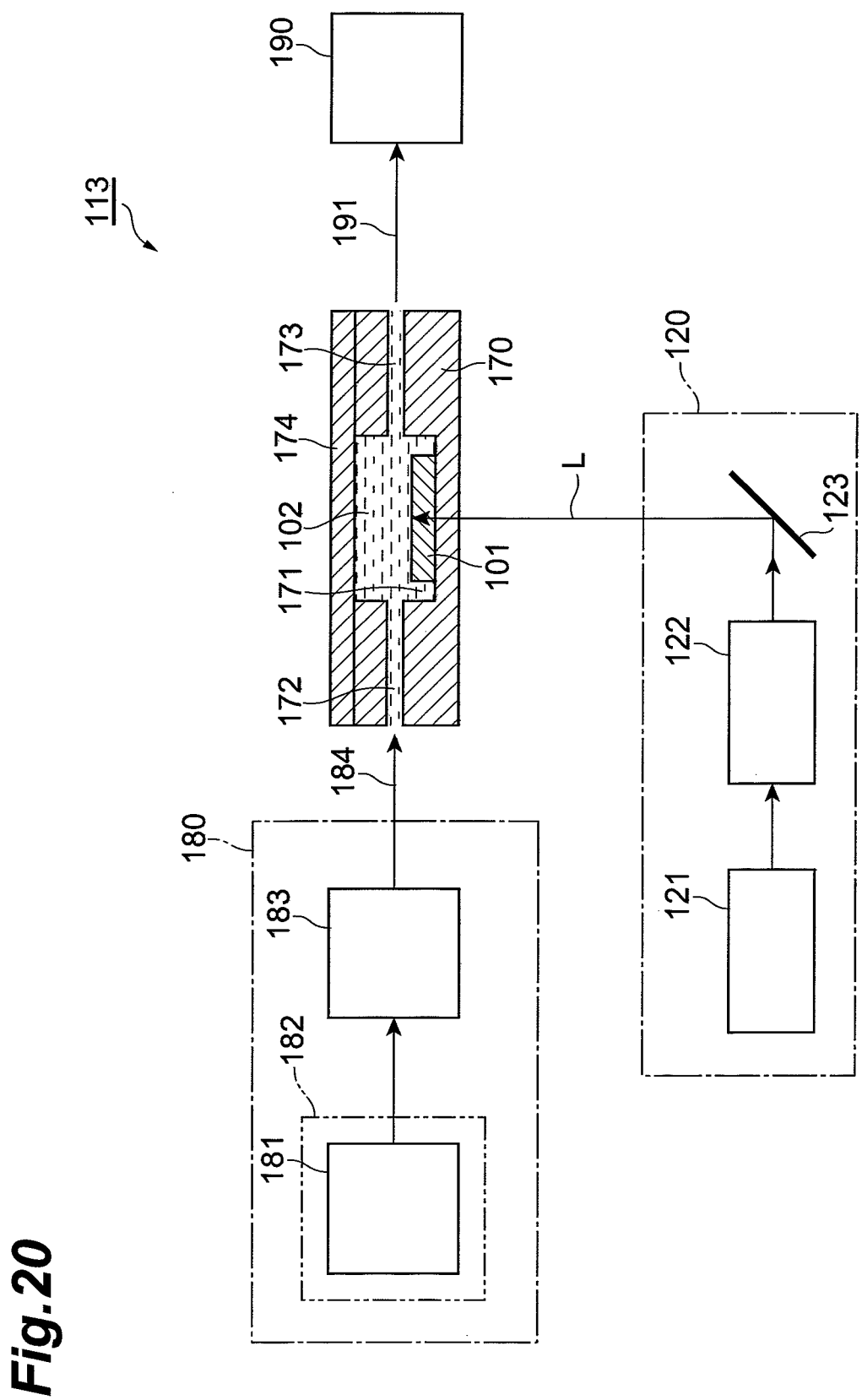
FIG. 20 is a configuration diagram of a microparticle dispersion liquid manufacturing apparatus 113 according to Embodiment 3B.

A microparticle dispersion liquid manufacturing method and a microparticle dispersion liquid manufacturing apparatus according to Embodiment 3B of the present invention shall now be described. FIG. 20 is a configuration diagram of the microparticle dispersion liquid manufacturing apparatus 113 according to Embodiment 3B. As shown in this figure, the microparticle dispersion liquid manufacturing apparatus 113 includes the light irradiating unit 120, a container 170, a water feeder 180, and a collector 190, and is for manufacturing a microparticle dispersion liquid having microparticles, containing a poorly soluble drug and a dispersion stabilizer, dispersed in water. The light irradiating unit 120 in Embodiment 3B has the same configuration as the light irradiating unit 120 in Embodiment 2B.

The container 170 used in Embodiment 3B is for containing the liquid to be treated, is composed of a material enabling transmission of a laser light L output from the light irradiating unit 120, and is preferably composed of glass. An inflow passage 172 and an outflow passage 173 are disposed between an internal space 171 of the container 170 and an exterior. When an upper plate 174 is mounted on the container 170, the internal space 171 and the exterior are connected only by the inflow passage 172 and the outflow passage 173. The figure shows a state where the residue 101 is fixed on a bottom surface of the internal space 171 of the container 170 and the water 102 is injected into the internal space 171 of the container 170.

The water feeder 180 is connected via a water feeding tube to the inflow passage 172 of the container 170, feeds water into the internal space 171 of the container 170, and thereby makes the water 102 flow near the interface of the residue 101 and the water 102 in the interior of the container 170. The water feeder 180, the inflow passage 172, and the water feeding tube 184 thus act as a water feeding unit that feeds water into the interior of the container 170 and as a flow unit that makes the water 102 flow near the interface of the residue 101 and the water 102 in the interior of the container 170.

The water feeder 180 includes a water feeding container 181, a temperature controller 182, and a water feeding pump 183. The water feeding container 181 contains water to be fed into the interior of the container 170. The temperature controller 182 maintains the water contained in the water feeding container 181 at a predetermined temperature, and the water of the predetermined temperature can thereby be fed into the interior of the container 170. The water feeding pump 183 feeds the water, contained in the water feeding container 181, to the inflow passage 172 of the container 170.

A peristaltic pump is preferably used as the water feeding pump 183. In this case, by immersing an inflow port of the water feeding pump 183 in the water in the water feeding container 181, the water is fed into the interior of the container 170. Also by placing the inflow port of the water feeding pump 183 in a gas (such as air), the gas is fed into the interior of the container 170. The water feeding pump 183 can thus also act as a gas feeding unit that feeds a gas into the interior of the container 170.

The collector 190 is connected by a drain tube 191 to the outflow passage 173 of the container 170 and collects and stores the microparticle dispersion liquid manufactured in the container 170. The collector 190, the outflow passage 173, and the drain tube 191 thus act as a collecting unit that collects the microparticle dispersion liquid manufactured in the interior of the container 170.

An operation of the microparticle dispersion liquid manufacturing apparatus 113 according to Embodiment 3B shall now be described along with the microparticle dispersion liquid manufacturing method according to Embodiment 3B. A flowchart for describing the microparticle dispersion liquid manufacturing method according to Embodiment 3B is the same as that shown in FIG. 15. A microparticle dispersion liquid, having microparticles, containing a poorly soluble drug and a dispersion stabilizer, dispersed in water, is manufactured by successively performing the dissolving step P1, the fixing step P2, and the irradiating step P3 in the microparticle dispersion liquid manufacturing method according to the present embodiment as well.

In the dissolving step P1, the poorly soluble drug and the dispersion stabilizer are dissolved in a volatile organic solvent in the container 170. Examples of the poorly soluble drug, the dispersion stabilizer, and the organic solvent have been mentioned above in regard to Embodiment 1B. In the fixing step P2, following the dissolving step P1, the organic solvent contained in the solution obtained in the dissolving step P1 is removed by evaporation, and by the organic solvent removal, a pellet-form residue 101 is obtained and this residue 101 becomes fixed on the bottom surface of the container 170.

After the fixing step P2, the upper plate 174 is mounted above the container 170, the water feeder 180 is connected via the water feeding tube 184 to the inflow passage 172 of the container 170, the collector 190 is connected via the drain tube 191 to the outflow passage 173 of the container 170, and the irradiating step P3 is performed.

In the water feeder 180 in the irradiating step P3, the water in the water feeding container 181, maintained at a fixed temperature by the temperature controller 182, is fed out by the water feeding pump 183. The water fed out from the water feeder 180 is fed into the internal space 171 via the water feeding tube and the inflow passage 172 of the container 170. The residue 101, fixed on the bottom surface of the internal space 171 of the container 170 is thereby immersed in the water 102. During a period in which the water is fed into the internal space 171 of the container 170 by the water feeding unit, the water 102 flows near the interface of the residue 101 and the water 102.

In this state in the irradiating step P3, the laser light L, output from the laser light source 121 is adjusted in both or either of the intensity and the irradiation duration by the irradiation light controller 122, reflected by the mirror 123, and irradiated on the residue 101 fixed on the bottom surface of the container 170. The residue 101 is thereby pulverized and made into microparticles, and a microparticle dispersion liquid, constituted of the microparticles being in the water 102, is thereby manufactured. The microparticles contain the poorly soluble drug and the dispersion stabilizer. The microparticle dispersion liquid, manufactured in the interior of the container 170, is transferred to and collected at the collector 190 via the outflow passage 173 and the drain tube 191.

With the microparticle dispersion liquid manufacturing apparatus 113 according to Embodiment 3B or the microparticle dispersion liquid manufacturing method according to Embodiment 3B, because the laser light L is irradiated at high efficiency on the pellet-form residue 101 fixed on the inner wall of the container 170, the microparticle dispersion liquid can be manufactured at high efficiency in a short time. Also preferably, an infrared pulse laser light of a wavelength of no less than 900 nm is emitted, and because the microparticles are formed even with a comparatively weak light irradiation of a degree with which multiphoton processes do not occur, drug degradation and other problems can be suppressed.

Also with the present embodiment, in the irradiating step P3, due to the feeding of water into the container 170 by the water feeding unit, the water 102 flows near the interface of the residue 101 and the water 102 in the interior of the container 170. Because the microparticles, formed by the irradiation of the laser light L, are thereby suppressed from being retained or accumulating near the interface of the residue 101 and the water 102, the formation of new microparticles by irradiation of the laser light L is not obstructed. Thus, the microparticle dispersion liquid can be manufactured at high efficiency in a short time from this aspect as well.

Microparticles, containing the poorly soluble drug and the dispersion stabilizer, are manufactured from the microparticle dispersion liquid manufactured and collected as described above. Or, lyophilized microparticles are manufactured by lyophilizing the microparticle dispersion liquid. Furthermore, an orally administered formulation, containing the microparticle dispersion liquid, the microparticles, or the lyophilized microparticles, is manufactured, or an injection formulation, containing the microparticle dispersion liquid or a dispersion liquid, obtained by resuspending the microparticles or the lyophilized microparticles in water, is manufactured.

Preferably in the irradiating step P3, the laser light L is irradiated from outside the region of the inner wall of the container 170 on which the residue 101 is fixed and the irradiated laser light L propagates in the order of the container 170, the residue 101, and the water 102 in the present embodiment as well. Preferably in the irradiating step P3, laser light L of a wavelength of no less than 900 nm is irradiated on the residue 101 from the light irradiating unit 120, and because the laser light L arrives at the interface via the residue 101 and the microparticles are formed at the interface, laser light L of a wavelength of low absorbance with respect to the residue 101 is preferably irradiated on the residue 101. Preferably in the irradiating step P3, both or either of the intensity and the duration of light irradiation on the residue 101 are or is adjusted by the irradiation light controller 122, and preferably during the light irradiation on the residue 101, the irradiated region or the interior of the container is maintained at a fixed temperature by the temperature controller 140. Preferably a sealed container is used as the container 170, and the dissolving step P1, the fixing step P2, and the irradiating step P3 are performed in a sterilized state.

107 The feeding of the water into the internal space 171 of the container 170 by the water feeding unit may be performed continuously or intermittently. In comparison to a case where the water is fed continuously, a microparticle concentration of the collected microparticle dispersion liquid is high and manufacture of injectable product is thereby facilitated in a case where the water is fed intermittently.

Also, the feeding of water by the water feeding unit and feeding of a gas by a gas feeding unit may be performed alternately and the microparticle dispersion liquid may be collected by the collecting unit during the feeding of the gas by the gas feeding unit. The microparticle concentration of the collected microparticle dispersion liquid is high and manufacture of injectable product is thereby facilitated in this case as well.

In a case where a capacity of the internal space 171 of the container 170 is adequately large, the collector 190 does not have to be disposed and the microparticle dispersion liquid obtained may be retained in the internal space 171 of the container 170. In this case, the water injected into the internal space 171 from the inflow passage 172 of the container 170 is preferably fed near the interface of the residue 101 and the water 102. The microparticle concentration near the interface of the residue 101 and the water 102 can thereby be maintained low efficiently.

EXAMPLE 1A

More specific examples of the microparticle dispersion liquid manufacturing apparatus or the microparticle dispersion liquid manufacturing method according to Embodiment 1A shall now be described.

Example 1A shall be described first. In Example 1A, a microparticle dispersion liquid of an immunosuppressant, cyclosporin A (hereinafter referred to as "CsA"), which is a poorly soluble drug, was prepared. CsA bulk powder (5 mg) as the poorly soluble drug and polyvinylpyrrolidone (25 mg) and sodium lauryl sulfate (1 mg) as dispersion stabilizers were placed in a test tube and dissolved in ethanol (500 μL), which is a volatile organic solvent. The solution was dispensed into each of the recesses 31 of the container 30, and the ethanol was dried under reduced pressure conditions to obtain mixtures (residues) of the drug and the dispersion stabilizers. The mixtures thus obtained were hermetically sealed upon adding water.

Nd:YAG pulse laser light was irradiated from below the container 30 on the mixtures fixed on the respective bottom surfaces of the recesses 31 of the container 30. The irradiation conditions were: a wavelength of 1064 nm; an irradiation light intensity of 0.61 J/cm$^2$/pulse; a pulse width of 5 to 7 ns; and a repetition frequency of 10 Hz. After 10 minutes of irradiation, a uniformly cloudy dispersion liquid was obtained upon shaking gently. In the present example, all operations were preformed under room temperature (20° C.).

Figure 11:
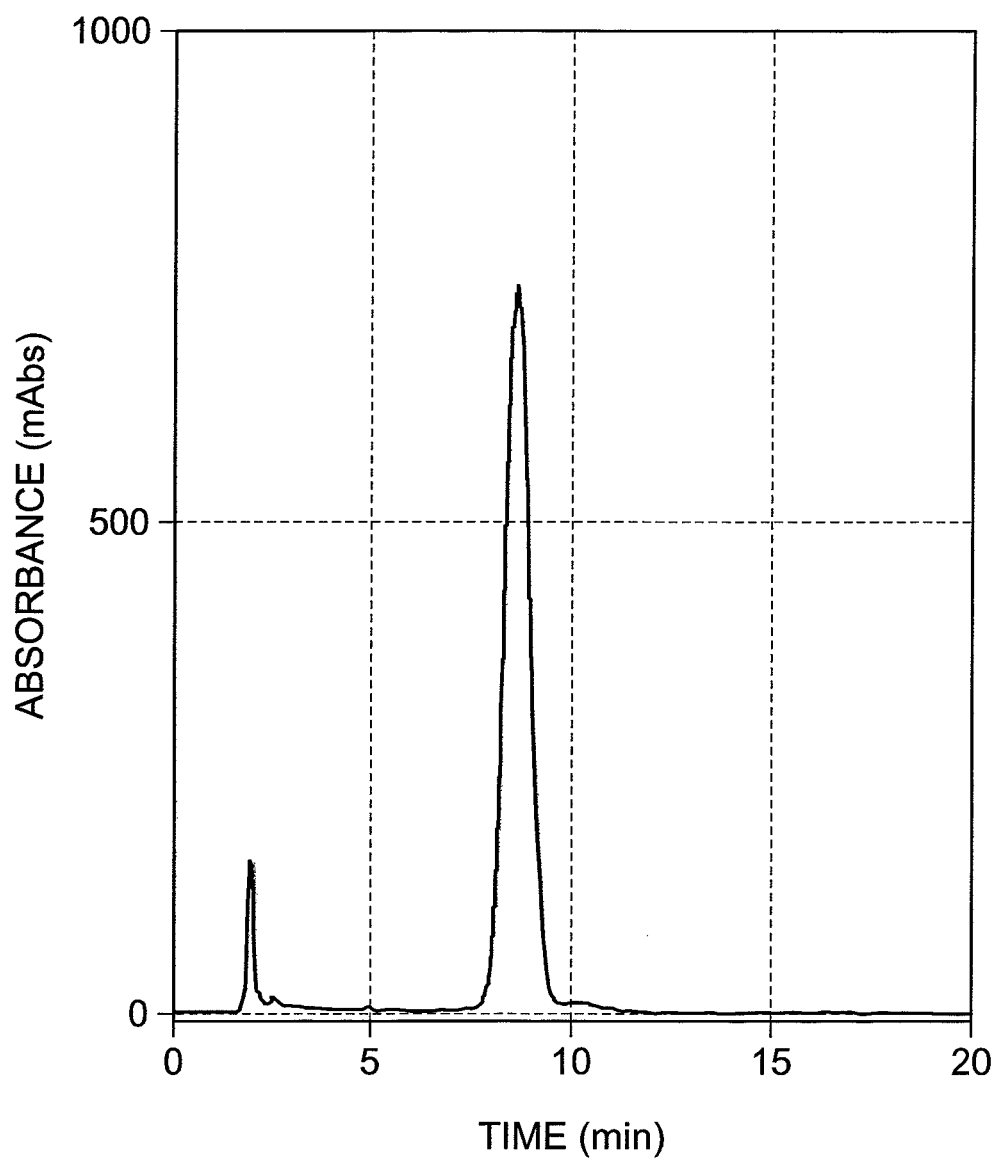
FIG. 11 is an HPLC chart of nanoparticulated cyclosporin A obtained in Example 1A.

A CsA amount contained in the dispersion liquid obtained was quantified by measuring an absorbance at a wavelength of 210 nm by using high performance liquid chromatography (hereinafter referred to as "HPLC"). ODS-C18 (manufactured by Tosoh Corp.) was used as a separation substrate and acetonitrile-isopropanol-water (2:5:3) was used as a mobile phase to perform the chromatography at a temperature of 50° C. A solution, prepared by dissolving CsA bulk powder in acetonitrile-water (1:1) to a concentration of 1 mg/mL, was used as a reference preparation. CsA was eluted at a position of approximately 8 minutes, and as a result of comparing and calculating the CsA amount in the sample based on a peak area obtained by measuring the reference preparation, the CsA amount in the microparticle dispersion liquid was found to be 8.24±0.05 mg/mL (n=3) (FIG. 11). It was thus possible to prepare a microparticle dispersion liquid with an adequately high concentration in comparison to a solubility (23 μg/mL) in water. Increase in impurity peaks due to laser irradiation was not observed on the HPLC chart.

Figure 12:
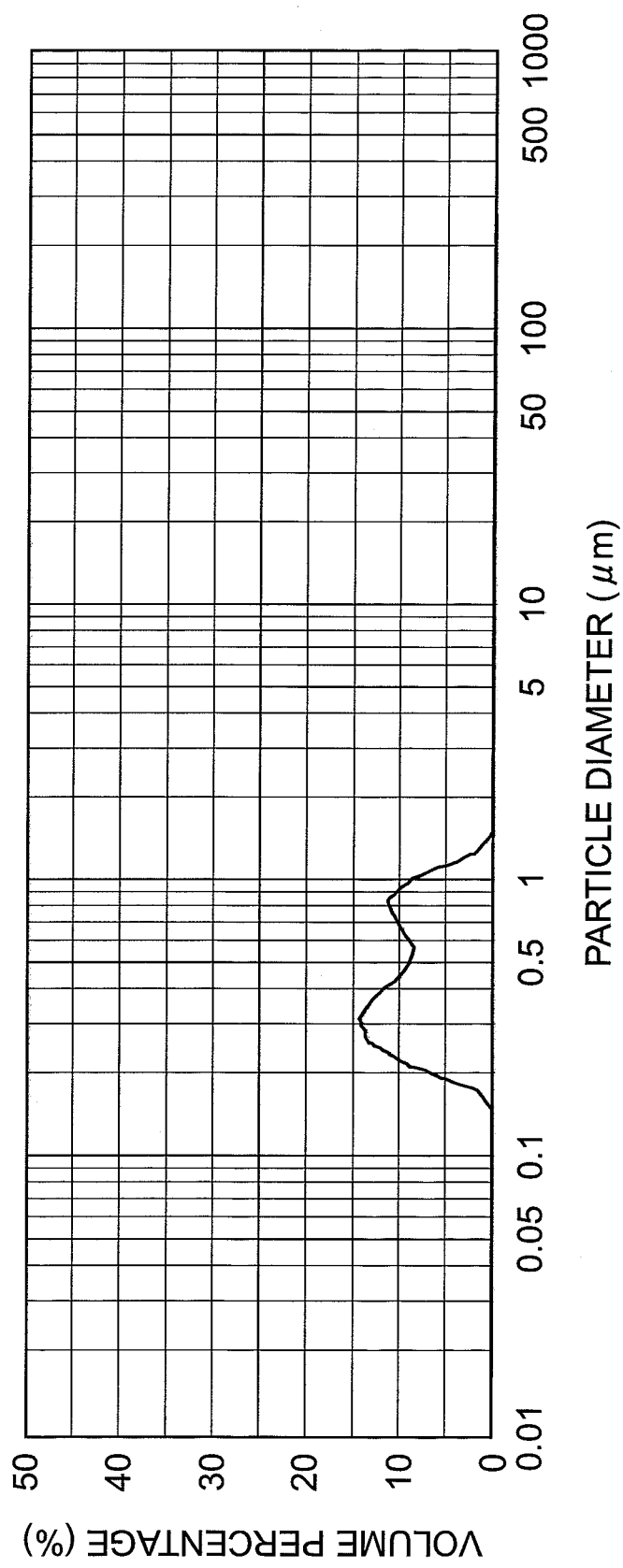
FIG. 12 is a diagram showing a particle diameter distribution of the nanoparticulated cyclosporin A obtained by Example 1A.

A particle size distribution of the microparticles contained in the microparticle dispersion liquid obtained in Example 1A was determined. SALD-7000 (manufactured by Shimadzu Corp.) was used as a measuring apparatus for particle diameter measurement. A particle size distribution, having a particle diameter range of 150 to 1500 nm and peaks at 300 nm and 800 nm, was obtained (FIG. 12). The dispersion liquid is thus considered to be a uniform microparticle suspension liquid of uniform particle size.

Figure 13:
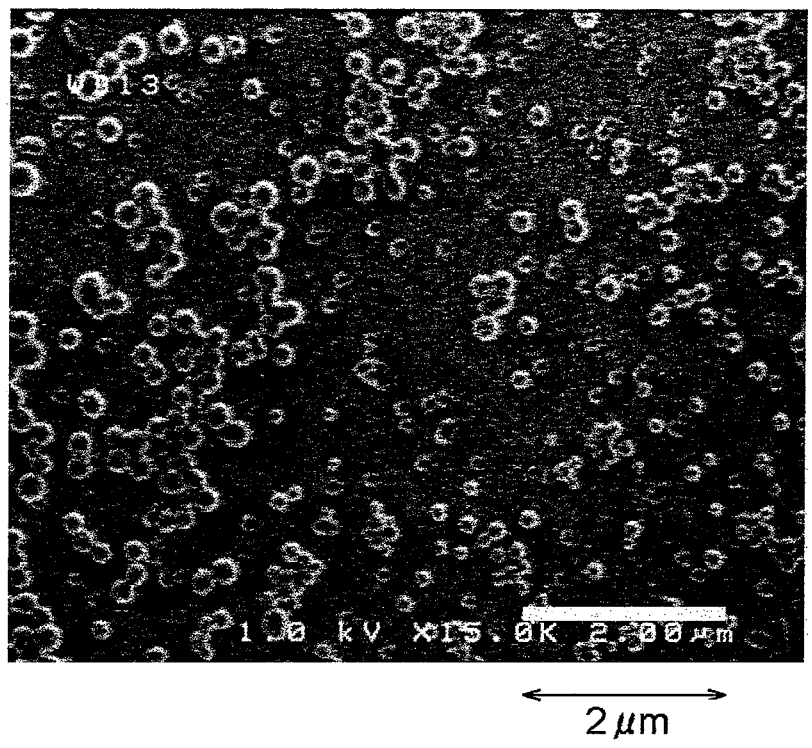
FIG. 13 is an electron microscope image of the nanoparticulated cyclosporin A obtained by Example 1A.

An electron micrograph of the microparticles contained in the microparticle dispersion liquid obtained in Example 1A was taken. A scanning electron microscope S4200 (manufactured by Hitachi, Ltd.) was used as a measuring apparatus. As can be seen from the photograph, the microparticles have a spherical shape and numerous microparticles with a particle diameter of approximately 200 to 300 nm were observed (FIG. 13). This matches the particle size distribution data by the HPLC and the microparticles are thus considered as being a uniform assembly of microparticles.

As described above, it was possible to prepare a microparticle dispersion liquid, in which CsA microparticles of uniform particle diameter, are dispersed. It was also possible to prepare microparticle dispersion liquids of different particle diameters by varying the liquid phase temperature during laser irradiation, the irradiation intensity, and the irradiation duration (refer to the following examples). Sedimentation was hardly observed even when the dispersion liquids obtained were left to stand still at room temperature for several days. Furthermore, lyophilization was possible, and significant differences in the particle size distribution and the electron microscopy image were not observed between the state before lyophilization and a resuspended dispersion liquid.

EXAMPLE 2A

Example 2A shall now be described. In Example 2A, poloxamer 407 (50 mg) was used as the dispersion stabilizer. Other manufacturing conditions and the microscopic observation conditions are the same as those of Example 1A. An electron micrograph of microparticles contained in a microparticle dispersion liquid obtained in Example 2A showed that the microparticles have a spherical shape and there are numerous microparticles with a particle diameter of no more than micrometer size.

EXAMPLE 3A

Example 3A shall now be described. In Example 3A, the intensity of the laser light irradiated on the mixture (residue) inside the test tube was set to 0.30 or 0.61 $J/cm^2/pulse$. Other manufacturing conditions and the microscopic observation conditions are the same as those of Example 1A. Electron micrographs of microparticles contained in microparticle dispersion liquids obtained in Example 3A showed that the microparticles have a spherical shape, the particle diameter varies according to the irradiation intensity, and the particle diameter is smaller in the case of lower irradiation light intensity. From these results, it is considered that the higher the irradiation light intensity, the larger the particle diameter of the microparticles formed.

EXAMPLE 4A

Example 4A shall now be described. In Example 4A, the duration of irradiation of the laser light on the mixtures (residues) fixed on the respective bottom surfaces of the recesses 31 of the container 30 was set to 10, 60, or 180 minutes. Other manufacturing conditions and the microscopic observation conditions are the same as those of Example 1A. Electron micrographs of microparticles contained in microparticle dispersion liquids obtained in Example 4A showed that the microparticles have a spherical shape and the particle diameter varies according to the irradiation duration. Whereas a large number of microparticles with a particle diameter of 200 to 500 nm were observed in the sample for which the irradiation duration was 10 minutes, a large number of microparticles with a particle diameter of 500 nm to 1 μm were observed in the sample for which the irradiation duration was 60 minutes, and a large number of microparticles with a particle diameter exceeding 1 μm were observed in the sample for which the irradiation duration was 180 minutes. From these results, it is considered that the longer the irradiation duration, the larger the particle diameter of the microparticles formed.

EXAMPLE 5A

Example 5A shall now be described. In Example 5A, an anti-inflammatory drug, clobetasone butyrate, was used as the poorly soluble drug and a microparticle dispersion liquid of clobetasone butyrate was prepared. Other manufacturing conditions, the particle size distribution measuring conditions and the microscopic observation conditions are the same as those of Example 1A. A particle size distribution and an electron micrograph of microparticles contained in the microparticle dispersion liquid obtained in Example 5A showed that the microparticles have a spherical shape, there are numerous microparticles with a particle diameter of no more than micrometer size, and the microparticles in the dispersion liquid are present within a range of 200 nm to 1 μm, and the dispersion liquid is thus considered to be a uniform microparticle suspension liquid of uniform particle size.

EXAMPLE 6A

Example 6A shall now be described. In Example 6A, an antiepileptic drug, nifedipine, was used as the poorly soluble drug and a microparticle dispersion liquid of nifedipine was prepared. Other manufacturing conditions and the particle size distribution measuring conditions are the same as those of Example 1A. A particle size distribution of microparticles contained in the microparticle dispersion liquid obtained in Example 6A showed that the microparticles in the dispersion liquid are present within a range of 200 nm to 2 μm, and the dispersion liquid is considered to have particle diameter peaks at 400 nm and 1.2 μm respectively.

EXAMPLE 7A

Example 7A shall now be described. In Example 7A, an anti-inflammatory drug, ibuprofen, was used as the poorly soluble drug and a microparticle dispersion liquid of ibuprofen was prepared. Other manufacturing conditions and the particle size distribution measuring conditions are the same as those of Example 1A. A particle size distribution of microparticles contained in the microparticle dispersion liquid obtained in Example 7A showed that the microparticles in the dispersion liquid are present within a range of 250 nm to 1 μm, and the dispersion liquid is thus considered to be a uniform microparticle suspension liquid of uniform particle size having a particle diameter peak at 700 nm.

EXAMPLE 1B

More specific examples of the microparticle dispersion liquid manufacturing apparatus or the microparticle dispersion liquid manufacturing method according to Embodiment 3B shall now be described.

Example 1B shall be described first. In Example 1B, a microparticle dispersion liquid of the immunosuppressant, cyclosporin A (hereinafter referred to as "CsA"), which is a poorly soluble drug, was prepared. CsA bulk powder (50 mg)

as the poorly soluble drug and polyvinylpyrrolidone (250 mg) and sodium lauryl sulfate (10 mg) as dispersion stabilizers were placed in a test tube and dissolved in ethanol (5 mL), which is a volatile organic solvent. The solution was placed in the container 170, and the ethanol was dried under reduced pressure conditions to obtain a mixture (residue) of the drug and the dispersion stabilizers. The mixture thus obtained was hermetically sealed upon adding water.

While feeding water into the container 170, Nd:YAG pulse laser light was irradiated on the mixture fixed on the inner wall of the container 170. The irradiation conditions were: a wavelength of 1064 nm; an irradiation light intensity of 0.61 J/cm$^2$/pulse; a pulse width of 5 to 7 ns; and a repetition frequency of 10 Hz. After 60 minutes of irradiation, a uniformly cloudy dispersion liquid was obtained. In the present example, all operations were performed under room temperature (20° C.).

Figure 21:
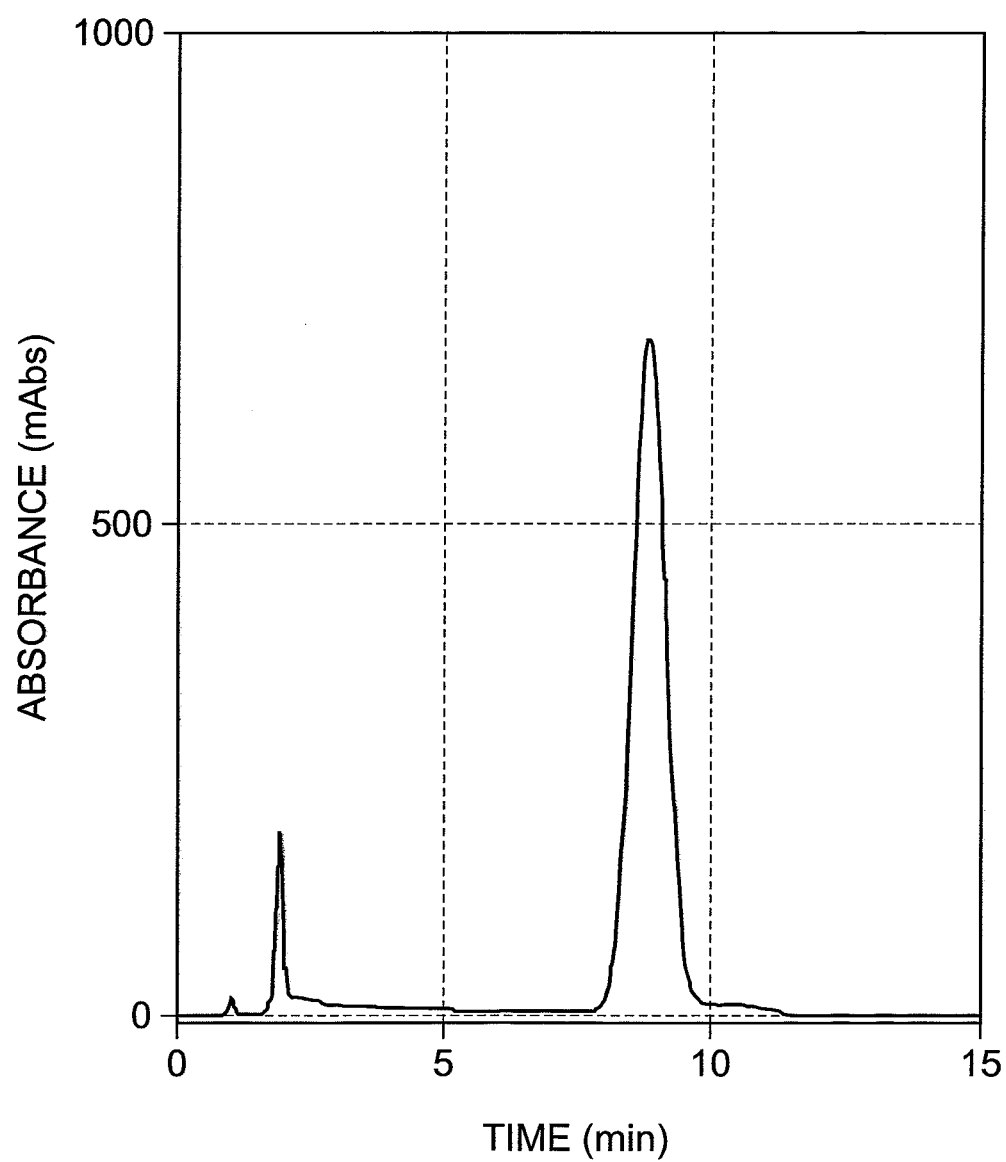
FIG. 21 is an HPLC chart of nanoparticulated cyclosporin A obtained in Example 1B.

The CsA amount contained in the dispersion liquid obtained was quantified by measuring the absorbance at the wavelength of 210 nm by using HPLC (FIG. 21). ODS-C18 (manufactured by Tosoh Corp.) was used as the separation substrate and acetonitrile-isopropanol-water (2:5:3) was used as the mobile phase to perform the chromatography at a temperature of 50° C. A solution, prepared by dissolving CsA bulk powder in acetonitrile-water (1:1) to a concentration of 1 mg/mL, was used as the reference preparation. CsA was eluted at a position of approximately 8 minutes, and as a result of comparing and calculating the CsA amount in the sample based on the peak area obtained by measuring the reference preparation, the CsA amount in the microparticle dispersion liquid was found to be 9.29±0.14 mg/nL (n=3). It was thus possible to prepare a microparticle dispersion liquid with an adequately high concentration in comparison to the solubility (23 μg/mL) in water. Increase in impurity peaks due to laser irradiation was not observed on the HPLC chart.

Figure 22:
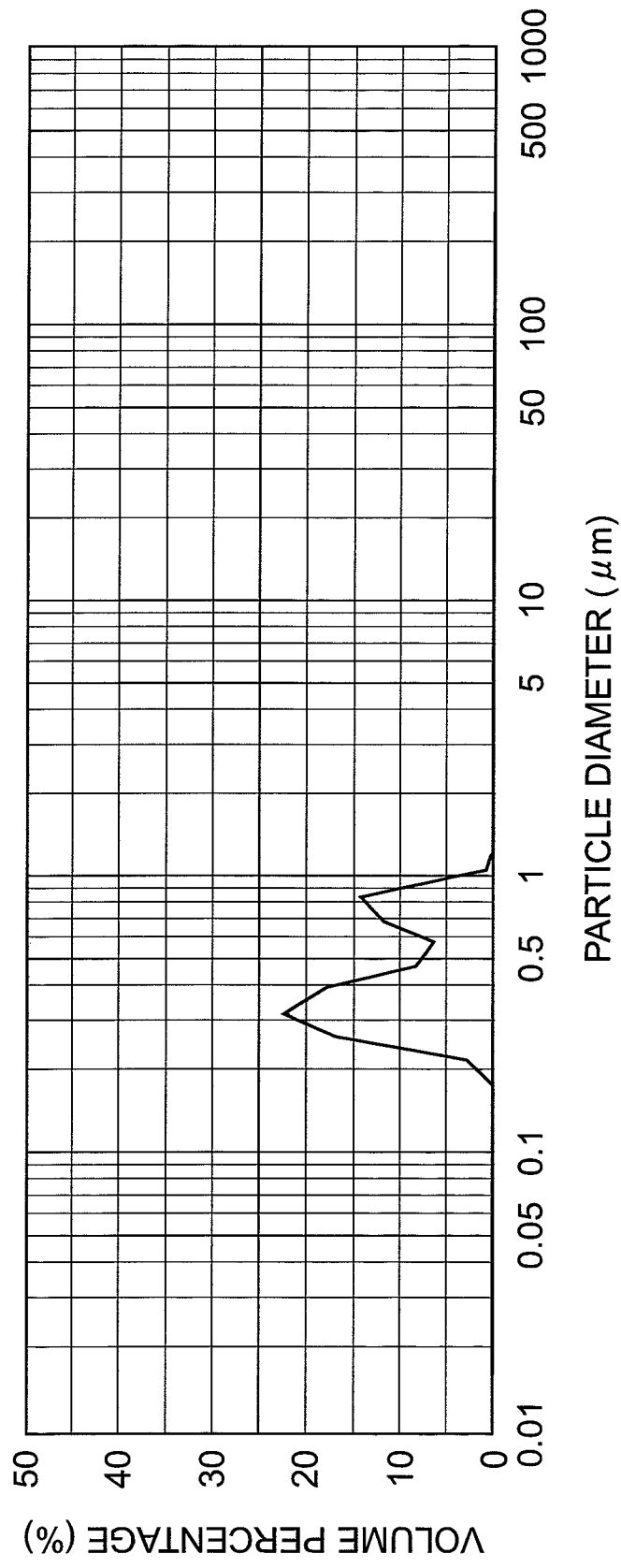
FIG. 22 is a diagram showing a particle diameter distribution of the nanoparticulated cyclosporin A obtained by Example 1B.

A particle size distribution of the microparticles contained in the microparticle dispersion liquid obtained in Example 1B was determined. SALD-7000 (manufactured by Shimadzu Corp.) was used as the measuring apparatus for particle diameter measurement. A particle size distribution, having a particle diameter range of 200 to 1000 nm and peaks at 300 nm and 800 nm respectively, was obtained (FIG. 22). The dispersion liquid is thus considered to be a uniform microparticle suspension liquid of uniform particle size.

Figure 23:
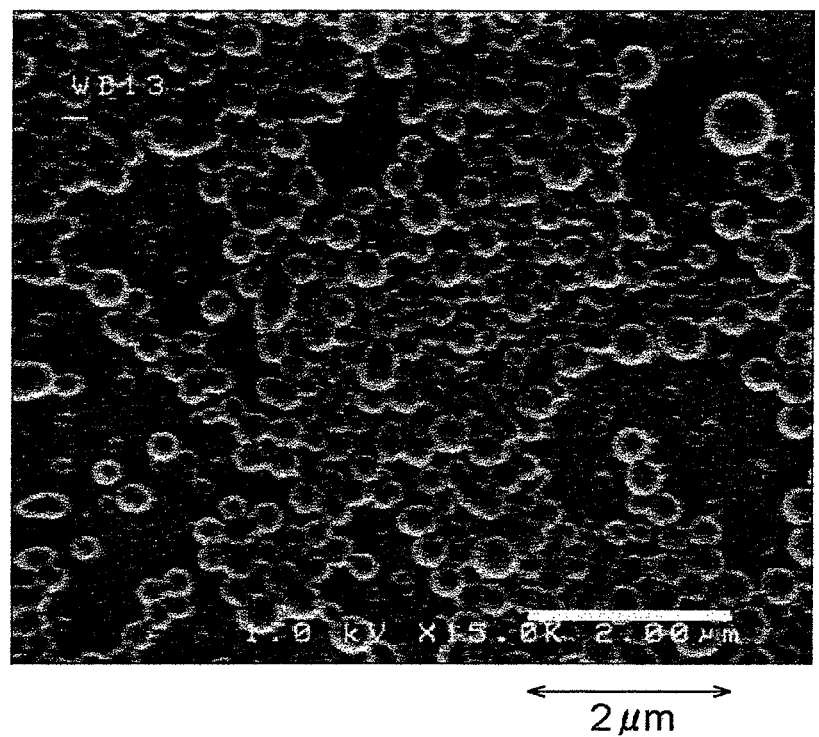
FIG. 23 is an electron microscope image of the nanoparticulated cyclosporin A obtained by Example 1B.

An electron micrograph of the microparticles contained in the microparticle dispersion liquid obtained in Example 1B was taken (FIG. 23). The scanning electron microscope S4200 (manufactured by Hitachi, Ltd.) was used as the measuring apparatus. As can be seen from the photograph, the microparticles have a spherical shape and numerous microparticles with a particle diameter of approximately 300 to 400 nm were observed. This matches the particle size distribution data and the microparticles are thus considered as being a uniform assembly of microparticles.

As described above, it was possible to prepare a microparticle dispersion liquid, in which CsA microparticles of uniform particle diameter, are dispersed. It was also possible to prepare microparticle dispersion liquids of different particle diameters by varying the liquid phase temperature during laser irradiation, the irradiation intensity, and the irradiation duration (refer to the following examples). Sedimentation was hardly observed even when the dispersion liquids obtained were left to stand still at room temperature for several days. Furthermore, lyophilization was possible, and significant differences in the particle size distribution and the electron microscopy image were not observed between the state before lyophilization and a resuspended dispersion liquid.

In general, microparticles of uniform and small particle diameter were obtained with the temperature of the water fed during laser light irradiation being lower. When the temperature of the water was set near 4° C., a dispersion liquid of microparticles of a uniform particle diameter of no more than 100 nm were obtained.

EXAMPLE 2B

Example 2B shall now be described. In Example 2B, poloxamer 407 (50 mg) was used as the dispersion stabilizer. Other manufacturing conditions and the microscopic observation conditions are the same as those of Example 1B. An electron micrograph of microparticles contained in a microparticle dispersion liquid obtained in Example 2B showed that the microparticles have a spherical shape and there are numerous microparticles with a particle diameter of no more than micrometer size.

EXAMPLE 3B

Example 3B shall now be described. In Example 3B, the intensity of the laser light irradiated on the mixture (residue) inside the test tube was set to 0.30 or 0.61 J/cm$^2$/pulse. Other manufacturing conditions and the microscopic observation conditions are the same as those of Example 1B. Electron micrographs of microparticles contained in microparticle dispersion liquids obtained in Example 3B showed that the microparticles have a spherical shape, the particle diameter varies according to the irradiation intensity, and the particle diameter is smaller in the case of lower irradiation light intensity. From these results, it is considered that the higher the irradiation light intensity, the larger the particle diameter of the microparticles formed.

EXAMPLE 4B

Example 4B shall now be described. In Example 4B, the duration of irradiation of the laser light on the mixture (residue) fixed on the inner wall of the container 170 was set to 10, 60, or 180 minutes. Other manufacturing conditions and the microscopic observation conditions are the same as those of Example 1B. Electron micrographs of microparticles contained in microparticle dispersion liquids obtained in Example 4B showed that the microparticles have a spherical shape and the particle diameter varies according to the irradiation duration. Whereas a large number of microparticles with a particle diameter of 200 to 500 nm were observed in the sample for which the irradiation duration was 10 minutes, a large number of microparticles with a particle diameter of 500 nm to 1 μm were observed in the sample for which the irradiation duration was 60 minutes, and a large number of microparticles with a particle diameter exceeding 1 μm were observed in the sample for which the irradiation duration was 180 minutes. From these results, it is considered that the longer the irradiation duration, the larger the particle diameter of the microparticles formed.

EXAMPLE 5B

Example 5B shall now be described. In Example 5B, the anti-inflammatory drug, clobetasone butyrate, was used as the poorly soluble drug and a microparticle dispersion liquid of clobetasone butyrate was prepared. Other manufacturing conditions, the particle size distribution measuring conditions and the microscopic observation conditions are the same as those of Example 1B. A particle size distribution and an electron micrograph of microparticles contained in the microparticle dispersion liquid obtained in Example 5B showed that the microparticles have a spherical shape, there are numerous microparticles with a particle diameter of no more than micrometer size, and the microparticles in the dispersion liquid are present within a range of 200 nm to 1 μm, and the dispersion liquid is thus considered to be a uniform microparticle suspension liquid of uniform particle size.

EXAMPLE 6B

Example 6B shall now be described. In Example 6B, the antiepileptic drug, nifedipine, was used as the poorly soluble drug and a microparticle dispersion liquid of nifedipine was prepared. Other manufacturing conditions and the particle size distribution measuring conditions are the same as those of Example 1B. A particle size distribution of microparticles contained in the microparticle dispersion liquid obtained in Example 6B showed that the microparticles in the dispersion liquid are present within a range of 200 nm to 2 μm, and the dispersion liquid is considered to have particle diameter peaks at 400 nm and 1.2 μm respectively.

EXAMPLE 7B

Example 7B shall now be described. In Example 7B, the anti-inflammatory drug, ibuprofen, was used as the poorly soluble drug and a microparticle dispersion liquid of ibuprofen was prepared. Other manufacturing conditions and the particle size distribution measuring conditions are the same as those of Example 1B. A particle size distribution of microparticles contained in the microparticle dispersion liquid obtained in Example 7B showed that the microparticles in the dispersion liquid are present within a range of 250 nm to 1 μm, and the dispersion liquid is thus considered to be a uniform microparticle suspension liquid of uniform particle size having a particle diameter peak at 700 nm.

EFFECTS OF THE INVENTION

With the present invention, a microparticle dispersion liquid can be manufactured with high efficiency in a short time. With the present manufacturing method, a residue fixed on an inner wall of a container, having a single, small-scale recess, is microparticulated reliably, the amount of the microparticle dispersion liquid obtained is increased by dramatically increasing the number of residues, and the microparticles are stabilized in shape and particle diameter and can be mass-produced.

Also with the present invention, because a microparticle dispersion liquid of high concentration can be manufactured, a poorly water-soluble drug, which heretofore has been applied as an intravenous preparation, can be applied as an injectable product, with which a necessary amount of effective components can be administered in a short time.

What is claimed is:

1. A microparticle dispersion liquid manufacturing apparatus comprising:
   a container having a mesh plate disposed to partition the interior of the container into upper and lower portions, configured for performing a process in which a poorly soluble drug and a dispersion stabilizer are dissolved in a volatile organic solvent, a residue, obtained by removal by evaporation of the organic solvent contained in the solution, is fixed on an inner wall of the lower portion of the container lower than the mesh plate, and water is injected into the upper portion of the container higher than the mesh plate;
   a light irradiating unit that irradiates light on the residue fixed on the inner wall on the lower portion of the container; and
   a flow unit that makes the water flow near an interface of the residue and the water in the interior of the container,
   wherein a microparticle dispersion liquid, having microparticles, containing the poorly soluble drug and the dispersion stabilizer, dispersed in water, is manufactured by the flow unit making the water flow near the interface of the residue and the water in the interior of the container and the light irradiating unit irradiating the light on the residue, and
   wherein the flow unit includes a stirring unit that is positioned on the mesh plate, that stirs the water injected into the upper portion of the container and makes the water flow near the interface of the residue and the water in the lower portion of the container.

2. A microparticle dispersion liquid manufacturing apparatus comprising:
   a container having a recess disposed at an annular region of a circumferential edge portion of the bottom surface, configured for performing a process in which a poorly soluble drug and a dispersion stabilizer are dissolved in a volatile organic solvent, a residue, obtained by removal by evaporation of the organic solvent contained in the solution, is fixed on the circumferential edge recess of the bottom surface of the container, and water is injected into an interior of the container;
   a light irradiating unit that irradiates light on the residue fixed on the circumferential edge recess of the bottom surface of the container; and
   a flow unit that makes the water flow near an interface of the residue and the water in the interior of the container, the flow unit being positioned above the circumferential edge recess of the bottom surface of the container,
   wherein a microparticle dispersion liquid, having microparticles, containing the poorly soluble drug and the dispersion stabilizer, dispersed in water, is manufactured by the flow unit making the water flow near the interface of the residue and the water in the interior of the container and the light irradiating unit irradiating the light on the residue, and
   wherein the flow unit includes a stirring unit that stirs the water injected into the interior of the container and makes the water flow near the interface of the residue and the water in the interior of the container.

* * * * *